US009927941B2

(12) United States Patent
Steimle et al.

(10) Patent No.: US 9,927,941 B2
(45) Date of Patent: Mar. 27, 2018

(54) METHOD FOR AGGREGATING TASK DATA OBJECTS AND FOR PROVIDING AN AGGREGATED VIEW

(71) Applicant: Roche Diagnostics Operations, Inc., Indianapolis, IN (US)

(72) Inventors: Anton Steimle, Rueti (CH); Urs Suter, Zurich (CH); Bernhard von Allmen, Seengen (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 655 days.

(21) Appl. No.: 13/752,688

(22) Filed: Jan. 29, 2013

(65) Prior Publication Data
US 2013/0145299 A1 Jun. 6, 2013

Related U.S. Application Data

(63) Continuation of application No. PCT/EP2011/063523, filed on Aug. 5, 2011.

(30) Foreign Application Priority Data

Aug. 5, 2010 (EP) .................................... 10172090

(51) Int. Cl.
G06F 3/048 (2013.01)
G06F 19/00 (2018.01)

(52) U.S. Cl.
CPC ............ *G06F 3/048* (2013.01); *G06F 19/366* (2013.01)

(58) Field of Classification Search
CPC ...... G05B 19/0426; G05B 2219/23258; G06F 8/34; G06F 9/4446; G06F 3/0481; G06F 3/04847
See application file for complete search history.

(56) References Cited

U.S. PATENT DOCUMENTS 5,832,475 A 11/1998 Agrawal et al.
5,909,217 A * 6/1999 Bereiter ........................ 715/854
(Continued)

FOREIGN PATENT DOCUMENTS

EP 1840576 A2 10/2007
JP H09-211003 A 8/1997
(Continued)

OTHER PUBLICATIONS

"Patient Safety Refresher—Universal Protocol", dated Dec. 2006 and downloaded from http://med.stanford.edu/shs/update/archives/DEC2006/boardpass.pdf on Aug. 19, 2016.*
(Continued)

*Primary Examiner* — Shourjo Dasgupta
(74) *Attorney, Agent, or Firm* — Roche Diagnostics Operations, Inc.

(57) ABSTRACT

A method implemented by an analysis system is presented. The method comprises receiving task data objects. At least some of the received task data objects are aggregated into aggregated task data object groups. All task data objects belonging to the same aggregated task data object group share at least one step of a task. A selectable aggregation GUI element is specified for each of the aggregated task data object groups. The aggregation GUI elements are displayed in an aggregated view on a graphical user interface. Upon selection of one of the aggregation GUI elements by a user, the aggregated task data object group represented by the selected aggregation GUI element is selected and the user access to program instructions for executing the shared step of the selected aggregated task data object group is automatically provided.

16 Claims, 18 Drawing Sheets

(56) References Cited

U.S. PATENT DOCUMENTS

| | | |
|---|---|---|
| 6,996,554 B2 | 2/2006 | Kotsis et al. |
| 7,627,671 B1* | 12/2009 | Palma et al. ............... 709/224 |
| 8,886,705 B1* | 11/2014 | Tewari et al. ............... 709/203 |
| 2003/0045958 A1 | 3/2003 | Brandt et al. |
| 2005/0210412 A1* | 9/2005 | Matthews ............ G06F 9/4443 |
| | | 715/835 |
| 2006/0080336 A1* | 4/2006 | Zhang et al. ............... 707/100 |
| 2006/0148063 A1* | 7/2006 | Fauzzi ............... G01N 1/31 |
| | | 435/286.4 |
| 2006/0178776 A1 | 8/2006 | Feingold et al. |
| 2006/0218030 A1* | 9/2006 | Ghosh et al. ............... 705/8 |
| 2007/0266136 A1* | 11/2007 | Esfahany ............ H04L 41/022 |
| | | 709/223 |
| 2008/0253298 A1* | 10/2008 | Bhatti et al. ............... 370/252 |
| 2009/0013287 A1* | 1/2009 | Helfman et al. ............ 715/853 |
| 2009/0094529 A1 | 4/2009 | Gonzalez et al. |
| 2009/0099871 A1 | 4/2009 | Gadodia |
| 2009/0164895 A1* | 6/2009 | Baeza-Yates et al. ........ 715/700 |
| 2009/0259493 A1* | 10/2009 | Venon et al. ............... 705/3 |
| 2010/0106603 A1* | 4/2010 | Dey et al. ............... 705/14.63 |
| 2011/0126123 A1* | 5/2011 | Reter et al. ............... 715/751 |
| 2011/0179231 A1* | 7/2011 | Roush ............... 711/152 |

FOREIGN PATENT DOCUMENTS

| | | |
|---|---|---|
| JP | H11-223634 A | 8/1999 |
| JP | 2004-310467 A | 11/2004 |
| JP | 2007-506975 A | 3/2007 |
| JP | 2008-051532 A | 3/2008 |
| JP | 2009-162584 A | 7/2009 |
| WO | 2006/057953 A3 | 6/2006 |
| WO | 2009/106081 A1 | 9/2009 |

OTHER PUBLICATIONS

"Comprehensive Procedure / Surgical Safety Checklist", dated Apr. 2015 and downloaded from http://cds.seton.net/i/495 on Aug. 19, 2016.*

International Search Report dated Mar. 14, 2012 in Application No. PCT/EP2011/063523, 3 pages.

* cited by examiner

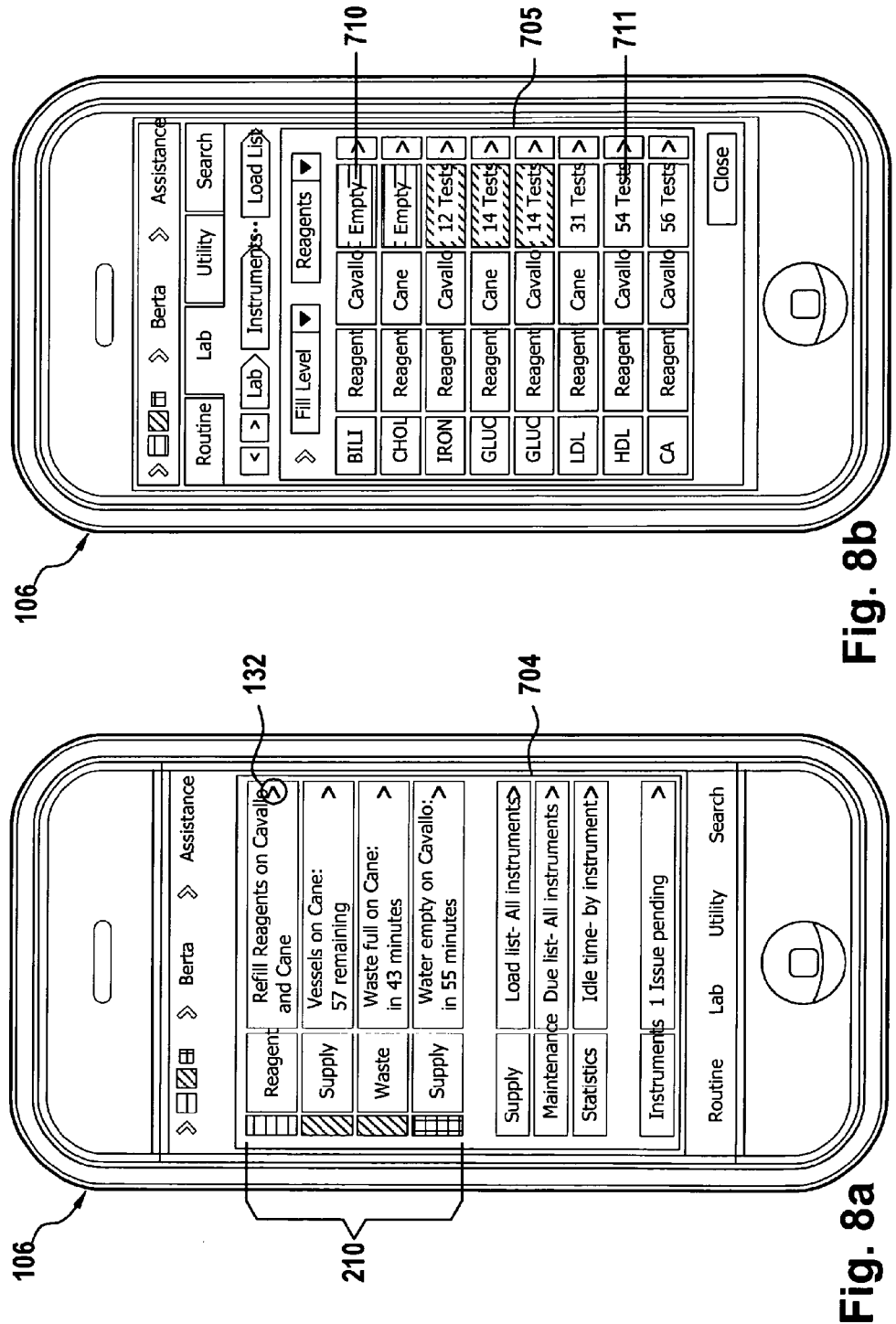

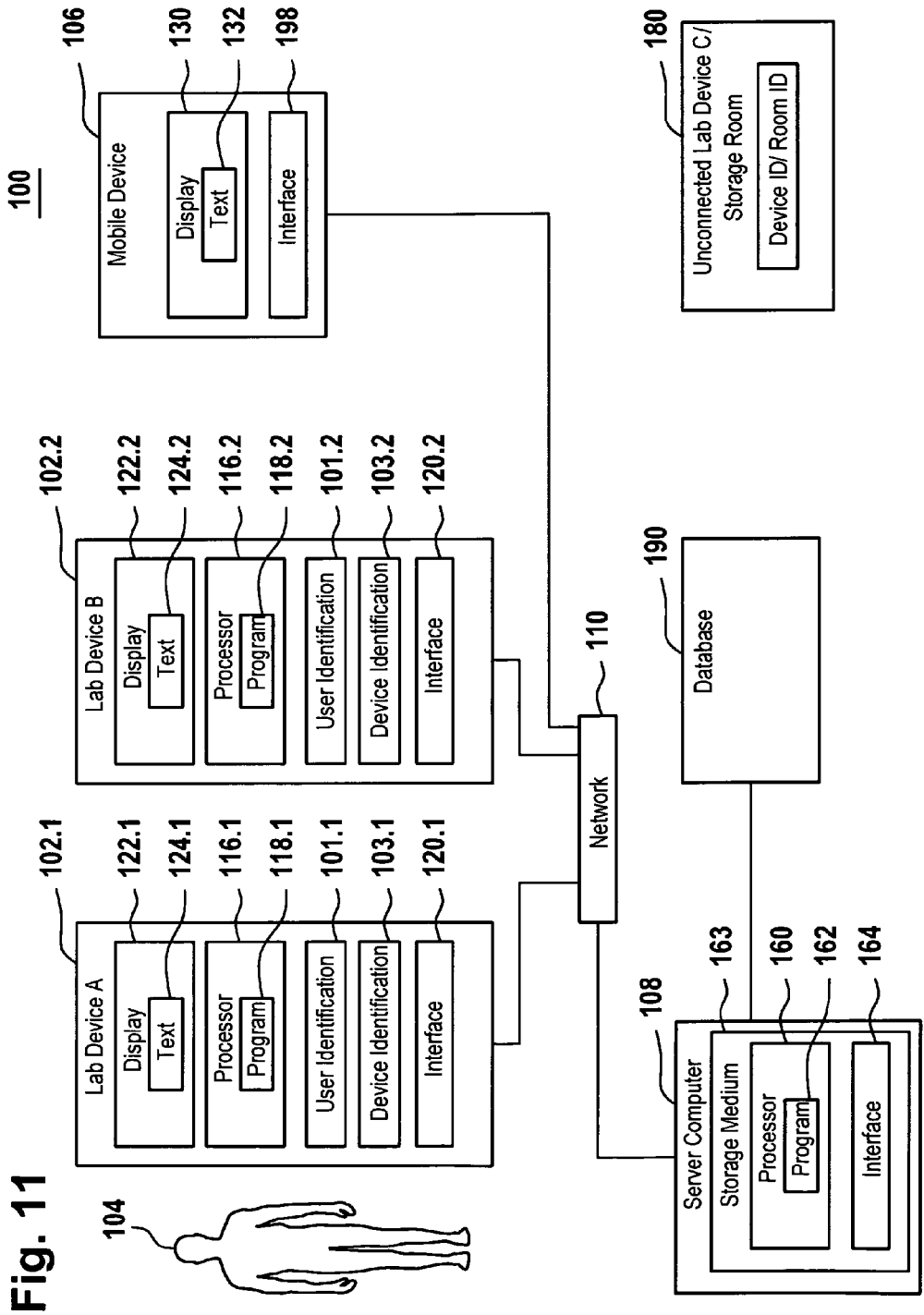

Fig. 15

METHOD FOR AGGREGATING TASK DATA OBJECTS AND FOR PROVIDING AN AGGREGATED VIEW

CROSS-REFERENCE TO RELATED APPLICATIONS

This application is a continuation of PCT/EP2011/063523, filed Aug. 5, 2011, which is based on and claims priority to EP 10172090.2, filed Aug. 5, 2010, which is hereby incorporated by reference.

BACKGROUND

The present disclosure generally relates to an analysis system and method for aggregating task data objects and, in particular to an analysis system and method for aggregating task data objects and providing an aggregated view, wherein at least some of the aggregated task data objects are indicative of a laboratory procedure.

In analytical laboratories, in particular clinical laboratories, a multitude of analyses on biological samples are executed in order to determine physiological and/or biochemical parameters being indicative of a disease, nutrition habits, drug effectiveness and/or organ function.

With the advent of new high-throughput technologies and advancement in lab automation systems, the number and complexity of tasks performed in parallel in a laboratory by a multitude of different lab devices has tremendously increased. While lab automation has helped to improve the quality of analysis results and to reduce payroll costs, lab automation has not rendered human interaction with automated or semi-automated laboratory workcell systems unnecessary. As lab automation allows performing a multitude of pre-analytical, analytical and/or post-analytical laboratory procedures in parallel by a multitude of different laboratory devices and/or laboratory workcell systems, a growing number of laboratory procedures executed in parallel has to be monitored and controlled.

Lab devices may fail or run out of reagents or other consumables. Often, a human is required to refill an empty reagent box, to replenish a consumable or to repair a failed lab device. In addition, in many cases, human interpretation of the gathered measurement values is still required. Although fewer lab workers are required to execute diagnostic or analytical tasks, a large number of highly diverse tasks related to monitoring and operating an analysis system and related to evaluating the gathered result still require human intervention.

Prior art laboratory workflow management systems allow the assignment of tasks to be performed in the context of a laboratory workflow to a particular user, thereby helping to clarify responsibilities in monitoring, controlling and/or executing tasks.

Therefore, there is a need for an improved analysis system, a computer-implemented method and a computer program product for displaying tasks which need to be performed in order to execute or complete a laboratory workflow which further assist a worker in efficiently executing assigned tasks and efficiently identifying and/or triggering actions which need to be performed in order to keep one or more monitored lab devices operative.

SUMMARY

According to the present disclosure, a method implemented by an analysis system is presented. The analysis system can be used for processing biological samples. The method can comprise receiving task data objects. Each task data object can comprise at least one attribute. At least some of the received task data objects can be indicative of a laboratory procedure to be performed by the at least one lab device. The at least one lab device can belong to the analysis system. At least some of the received task data objects can be aggregated into aggregated task data object groups. All task data objects belonging to the same aggregated task data object group can share an attribute value or value range of the at least one attribute. The at least one shared attribute value or value range can be indicative of at least one shared step of the task of the attribute's task data object. The shared step can be shared by all tasks of the task data objects of the aggregated task data object group. A selectable aggregation graphical user interface (GUI) element can be specified for each of the aggregated task data object groups. The aggregation GUI element can represent the aggregated task data object group. The aggregation GUI elements can be displayed in an aggregated view on a graphical user interface. Upon selection of one of the aggregation GUI elements by a user, the aggregated task data object group represented by the selected aggregation GUI element can be selected and the user access to program instructions for executing the shared step of the selected aggregated task data object group can automatically be provided.

Accordingly, it is a feature of the embodiments of the present disclosure to provide an improved analysis system, a computer-implemented method and a computer program product for displaying tasks which need to be performed in order to execute or complete a laboratory workflow which further assist a worker in efficiently executing assigned tasks and efficiently identifying and/or triggering actions which need to be performed in order to keep one or more monitored lab devices operative. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 8a illustrates the screen of a mobile device displaying a first pane according to a first display mode, the first pane comprising a tasks pane and a favorites pane according to an embodiment of the present disclosure.

FIG. 8b illustrates the screen of the mobile device displaying a second pane according to the first display mode, the second pane providing an aggregated view generated as the result of a drill-down analysis according to an embodiment of the present disclosure.

FIG. 11 illustrates a block diagram of an embodiment of an analysis system of the invention according to an embodiment of the present disclosure.

FIG. 15 illustrates a screenshot of two window panes for displaying and/or executing supply related tasks according to an embodiment of the present disclosure.

DETAILED DESCRIPTION

Figure 1:
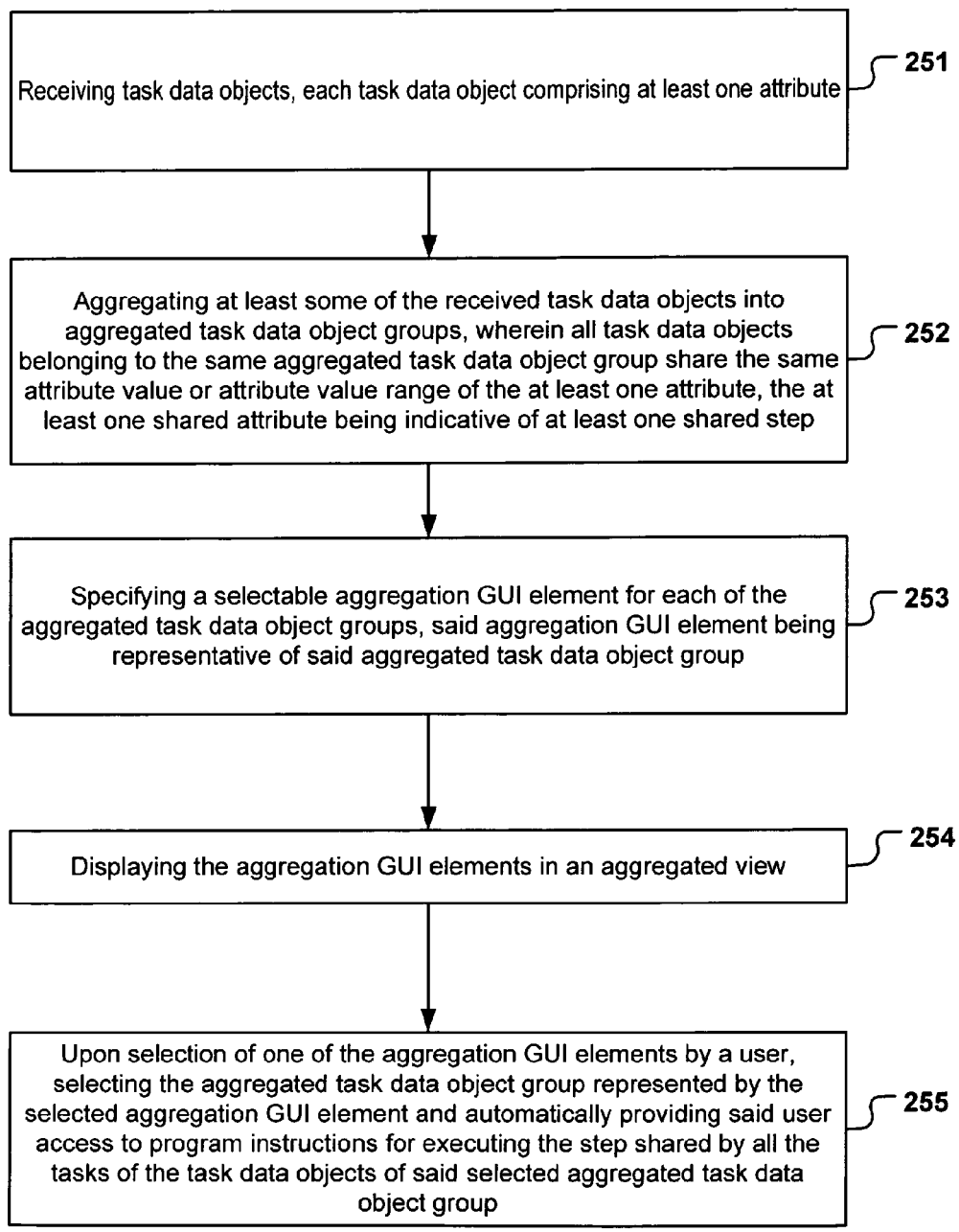
FIG. 1 illustrates a flow chart of a method providing an aggregated view according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The term "lab device" as used herein can encompass any pre-analytical, analytical and/or post-analytical laboratory device which performs a laboratory workflow step on one or more biological samples. A lab device can be, for example, a centrifuge, a capping- or decapping unit, a sample storage unit, a conveyor belt, an analyzer, an aliquoter, a photometer or the like. A lab device can be an analyzer or a receptacle of a sample, an analytical adjuvant material, a reagent, a wash buffer, an auxiliary liquid, a pipette, pipette tip or bulb or the like. A lab device can also be any decapper device, a sample preparation and distribution system, a post-analytical device, in particular an automated sample storage device, and the like.

The term "analysis system" as used herein can encompass any system of lab devices which can operate and/or monitor collectively. Typically, but not necessarily so, an analysis system can comprise one or more analyzers, but the term "analysis system" may also refer to a system comprising only one or more pre-analytical and/or post-analytical devices. For the sake of simplicity, the systems of lab devices can herein also refer to as "analysis systems."

An "analyzer" can be a laboratory apparatus that can analyze a reaction of a biological sample with a reagent for obtaining a measurement value. For example, an analyzer can measure light absorption, fluorescence, electrical potential or other physical or chemical characteristics of the reaction to provide the measurement data.

The term "mobile device" as used herein can encompass any mobile electronic appliance having an interface for communicating with a server computer, in particular any handheld battery powered mobile appliance, such as a mobile phone, a smart phone, a personal digital assistant (PDA) or another electronic appliance having a wireless interface for establishing a communication link with a server computer such as over a wireless digital cellular telecommunications network or another wireless communication channel.

The term "drill-down analysis" as used herein can refer to the execution of data processing and data evaluation techniques including, for example, arithmetic and/or statistical calculations on a set of data objects. The execution of the drill-down analysis can be triggered by a user navigating among levels of data ranging from the most aggregated (up) to the most detailed (down).

The term "data aggregation" as used herein can be any process in which information can be gathered and grouped together. Data aggregation can allow the gathering of information about particular data objects sharing one or more specific attributes.

A "task" as used herein can encompass any laboratory procedure performed, for example, on one or more biological samples, by a lab device. In addition, the term can encompass any operation performed on data being received from one or more lab devices of an analysis system upon processing a biological sample. The term further can encompass any processing executed by a worker on a lab device in order to preserve or restore the operability of a lab device. Accordingly, executing a task can comprise executing a pre-analytical, analytical or post-analytical workflow or workflow by a lab device, for example, an analyzer or a centrifuge. Executing a task can also comprise evaluating measurement values obtained on one or more samples by a user, for example, by means of a GUI, or refilling an empty reagent container of a lab device by the user.

The term "task data object" as used herein can encompass any data object indicative of a task. In particular, the term can refer to data objects indicative of a laboratory procedure performed on one or more biological samples using one or more lab devices. A task data object can be, for example, an instance of a class object specified in an object oriented programming language such as Java or C#.

A "consumable" as used herein can be any liquid, material or device component needing a refill or replacement action on a regular basis while operating one of the lab devices. A consumable can be, for example, a reagent, a calibration liquid or a cuvette for executing optical measurements.

Executing an aggregation based on a shared task may advantageous for the following reason: the user may be less disturbed by 'visual noise' as the tasks are not displayed in list form but rather can be displayed in the form of a comparatively small number of aggregation graphic user interface (GUI) elements.

Further, the feature that the aggregation GUI elements can be selectable and that a selection of one of the aggregation GUI elements can automatically provide the user access to program instructions for executing the shared step of the selected aggregated task data object group may be advantageous, because the user can immediately reach program instructions for executing all aggregated tasks of the selected aggregation GUI element. The shared step can be executed at a shared physical location, for example, a particular building or room or a particular lab device. The shared step may likewise relate to program instructions which can be shared by all tasks represented by the task data objects of one aggregated task data object group. The shared program instructions may allow executing or beginning to execute— at one shared physical or logical position within a workflow—a particular step within the workflow. The shared program instructions may specify a shared workflow execution view, may specify a shared program routine or a shared command for operating some of the lab devices.

For example, the display of a workflow execution view may be triggered, the view enabling a user to execute a plurality of evaluation tasks by one and the same GUI content. Thus, the user may not have to switch between different views for executing the same task. Likewise, the workflow evaluation view may comprise an indication of a plurality of maintenance tasks aggregated according to the shared task step of retrieving consumables for refilling the lab devices from one particular storage room, thereby enabling a user to go to the storage room only once, thereby picking up all consumables required to fill up a plurality of different lab devices. Prior art systems wherein tasks are presented to a user in list form are less efficient, as the user would simply execute refill actions in accordance with a chronologically or otherwise sorted list of tasks. A 'maintenance' task as used herein can encompass any task of inspecting and/or repairing a lab device for ensuring that the lab device remain operative or becomes operative again after a failure, it further can encompass tasks where consumables as reagents, disposable pipette tips, cuvettes and so on are loaded or waste is eliminated.

In accordance with some embodiments, task data objects can be received by a server computer. Depending on the embodiment, the task data objects may be received from a single or a plurality of sources. According to some embodiments, a relational database having stored therein one or more task data objects can be used as source. The database may be stored on a storage medium of the server computer or may be stored on a remote database server accessible by the server computer via a network, for example, the intranet of a laboratory. The database may also be implemented as a multitude of different databases hosted on one or more different computers. According to some embodiments, the database may also be an integral part of a lab device belonging to the analysis system.

Depending on the embodiment, the server computer can be a server, or any other kind of standalone processing device, connected to at least one lab device of the analysis system. According to some embodiments, the server computer can be an integral component of the analysis system. According to further embodiments, the server computer can be an integral component of a lab device of the analysis system. According to still further embodiments, the functionality provided by the server computer can be accessed by other computers, in particular end user computers. Access can be provided, for example, in via the middleware, for example, a workflow management system, or via the laboratory information system (LIS) of a laboratory.

According to some embodiments, at least some of the task data objects can be received dynamically from a lab device of an analysis system. The lab device can be connected to the server computer via a network, for example, an Intranet of a laboratory.

According to some embodiments, at least some of the task data objects can represent a test request and can be received from a lab device or from a further computer. The lab device or the further computer can allow a user to specify a test request. A test request can be, for example, a request to perform a particular analysis, for example, an analysis determining the blood glucose concentration of a sample of a particular patient. The test request can be represented as task data object and can be transmitted to the server computer. The further computer may be, for example, a computer of a physician. The computer of the physician can be connected to the server computer via a network, for example, the intranet of the laboratory or the Internet.

According to some embodiments, at least some of the task data objects can be received dynamically from a lab device and can represent tasks which have to be performed on the lab device in order to restore or preserve its operability. For example, an analyzer requiring a particular reagent for executing an analysis which has run out of reagent can submit a request to refill the container of the reagent to the server computer.

According to further embodiments, the task data objects received by the server computer from a lab device can be indicative of an error state of the lab device and/or can be indicative of the task required to restore operability of the device. According to further embodiments, the task data objects received by the server computer from the one or more lab devices can comprise additional information on how the indicated task can be executed by a user. A task data object indicative of the task to refill a particular reagent for a particular lab device may comprise, for example, data on the position of the lab device, for example, the room number and/or an identifier of the laboratory to which the lab device belongs. The task data object may in addition or alternatively comprise data on the lot number of the reagent, on the storage room where a new bottle of reagent can be retrieved, on the shelf-life of the reagent and the like.

Depending on the embodiment, receiving one or more task data objects can be executed via a push- or pull method or a combination thereof. According to some embodiments, the server computer can retrieve task data objects stored in the relational database via the pull method on a regular basis. In addition, task data objects dynamically generated by a user in the form of, for example, a test request or dynamically generated by a lab device, for example, in the form of an error or status message may be submitted from the lab device to the server computer and/or the relational database via the push method.

Program modules managing the data exchange between server computer, the one or more lab devices and the one or more sources for receiving the task data objects can be, according to an embodiment, integrated into the middleware of a laboratory or can be integrated into a LIS.

At least some of the received task data objects can be indicative of a laboratory procedure to be performed by at least one lab device. A laboratory procedure can be any pre-analytical, analytical or post analytical step of a laboratory workflow, including multiple steps of a workflow, to be executed on one or more biological samples. A biological sample can be, for example, a blood or serum sample of a patient. A biological sample may also be a multi-well plate, tissue slides, cell cultures, chip assays or the like.

Each of the received task data objects can comprises one or more attributes. An attribute can be, for example and without limitation:
- the type of the indicated task (for example, lab device maintenance, requested analytical tests, evaluation of measurement results);
- an urgency level of the indicated task; an urgency level can indicate the urgency and priority of a task. Highly urgent tasks can require immediate action of a user in order to preserve operability of the analysis system.
- the time at which the indicated task is to be executed, for example, a particular date or time;
- an identifier of a physical location where the indicated task is to be executed, whereby the physical location can be, for example:
    - a device-ID indicative of a lab device, the lab device performing the indicated task,
    - an identifier of a component of a lab device assigned to the indicated task, for example, a calibrating unit being integral part of an analyzer,
    - a specification of a place the lab device is located at, the lab device to perform the indicated task; the specification can be, for example, a room number and/or an identifier of a laboratory,
    - a specification of a place a biological sample is stored in or can be retrieved from, the biological sample to be processed in the indicated task,
    - a storage-room-ID and/or a storage device-DI of the room or device wherein a reagent used for executing the indicated task is stored,
- an identifier of a set of program instructions for executing the indicated task, whereby the program instructions can be, for example:
    - an identifier indicative of a GUI pane comprising GUI elements for evaluating analysis results obtained on biological samples,
    - an identifier indicative of a GUI pane comprising GUI elements displaying messages on hardware failures in one of the at least one lab device,
    - an identifier indicative of a GUI pane comprising GUI elements for displaying a manual how a detected hardware error can be fixed,
- a user-ID of a user assigned to the indicated task,
- a role-ID of a user role assigned to the indicated task,
- a group-ID of a user assigned to the indicated task,
- an identifier of the type of the indicated task,
- a pre-analytical, analytical or post-analytical procedure performed according to the indicated task, for example, the determination of the glucose level in a blood sample,
- a type of a reagent used for executing the indicated task,
- a supplier ID of the supplier of a reagent used for executing the indicated task, and
- a patient-ID of the patient providing the biological sample to be processed during the indicated task.

Depending on the embodiment and on the attribute(s) used for aggregation, the created aggregated task data object groups can be disjoint or overlapping in respect to the task data objects contained therein.

According to some embodiments, at least some of the task data object groups respectively can comprise an aggregated data value. The aggregated data value can be calculated from all task data objects contained in the aggregated task data object group. The calculation may use all or parts of the data contained in each task data object belonging to the aggregated task data object group. The calculation of the aggregated data value can comprise, for example, executing a mathematical function on one or more data values of all task data objects belonging to an aggregated task data object group, thereby returning an aggregated data value as result. The mathematical function may comprise, for example, the calculation of a minimum or maximum value, the calculation of a sum or any combination of the or another mathematical operation. The calculated data value may also be the number of task data objects contained in a particular aggregated task data object group. The number may be displayed by the GUI element representing the aggregated task data object group.

According to embodiment, each selectable aggregation GUI element can provide the user access to program instructions for executing the tasks indicated by the task data objects represented by the aggregation GUI element. For example, tasks aggregated together into one aggregated task data object group can be validation tasks performed on a particular kind of measurement result, for example, by manual inspection of the obtained measurement values and/or by a visual inspection of plots having been automatically generated based on the measurement values. Accordingly, a shared task step may be the display of one out of a plurality of available workflow execution views which can comprise GUI elements enabling a user to evaluate a particular type of measurement value. The GUI elements can be, for example, text labels, buttons, evaluation functions, statistical graphs of analytical test results and the like. According to another example, the aggregated tasks may also be a set of calibration tasks. A calibration task may comprise the task of calibrating one of the lab devices. A shared step of the calibration task can be executing the calibration at lab devices located at the same location, for example, the same room, department or lab. Thus, the user can execute the tasks more efficiently because all calibration tasks to be executed for example, in the same room can be bundled. A task may also be the maintenance of a plurality of lab devices sharing the same location. The location may be indicated by the at least one attribute of each task data object, for example, a room-ID.

A graphical user interface element (GUI element) can be specified for each of the aggregated task data object groups whereby an aggregated data representation may be displayed for each of the aggregated task data object group and may be used for specifying the aggregation GUI element of the aggregated group.

A 'view' can be a particular type of arrangement of one or more elements on a graphical user interface. An "aggregated view" can be a view comprising at least one aggregated task data object. Thus, an aggregated view can provide the user with an intuitive and quickly comprehensible presentation of all or some of the tasks represented by a multitude of aggregated data objects. Providing an aggregated view can comprise displaying one or more GUI elements respectively representing an aggregated task data object group. In addition, an aggregated view may comprise additional GUI elements showing the user the number of data objects aggregated, an aggregated priority score, or any other form of aggregated data value. The aggregated data value may be displayed as alphanumerical character, may be encoded by a color schema or may be encoded by using a set of predefined images. The aggregated data value may be displayed, for example, as integral part of the GUI element representing the aggregated task data object group for which the aggregated data value was calculated.

A GUI element can be a data object whose attributes specify the shape, layout and/or behavior of an area displayed on a graphical user interface, for example, a screen. A GUI element can be a standard GUI element such as a button, a text box, a tab, an icon, a text field, a pane, a check-box item, item group or the like. A GUI element can likewise be an image, a displayed alphanumeric character or any combination thereof. An aggregated data value generated in the aggregation step may be used, for specifying a GUI element implies that at least some of the properties of the displayed GUI elements depend on the aggregated data value. According to some embodiments, the aggregation GUI element can comprise a numerical value indicative of the total number of task data objects of the aggregation data object group.

According to some embodiments, each task data object can have assigned a user- or group-ID. The tasks data objects can be grouped into groups sharing the same user-based on this ID. The aggregating of the task data objects can be selectively executed for the group of task data objects having assigned the user- or group-ID of a logged-in user.

According to other embodiments, each task data object can be assigned a user- or group-ID. The tasks data objects can be filtered based on this ID. The aggregating of the task data objects can be selectively executed for the group of task data objects having assigned the user- or group-ID of a logged in user.

According to some embodiments, the aggregated GUI element can comprise a numerical value indicative of the total number of tasks to be executed by a lab device identified by a shared device-ID. The shared device-ID can be indicative of the shared task step. Alternatively, or in addition, the aggregation GUI element can be an image indicative of the lab device or type of the lab device whose device-id can be assigned to the aggregated task data objects, thereby facilitating a user to identify the lab device where the tasks indicated by the aggregated task data objects to be performed. Instead of or in addition to a lab device-ID, a component-ID of the lab device may be used for aggregation.

According to some embodiments, the aggregation GUI element can be indicative of the lab device-component having assigned the device-component-ID. By highlighting, or otherwise optically accentuating, the identified device-component where a task needs to be performed, the identification of the lab device-component by a user for performing the tasks indicated by the task data objects can be greatly facilitated.

According to some embodiments, an analyzer can comprise one analysis component and one or more reagent components. Each reagent component can comprise at least one reagent container. In the case where the reagent container of the first reagent component runs out of reagent, the aggregation of task data objects according to the attribute 'device-component-ID' results in the provision of an aggregated view, the analysis system can be represented and displayed on a graphical user interface as a schematic diagram. The schematic diagram can represent the analyzer- and reagent components as distinct areas. According to the embodiments, the task of refilling the reagent of the first reagent component can be represented as a task data object. The task data object can assign the device-component-ID of the first reagent component. Upon aggregating task data objects according to their assigned device-component-IDs, the aggregated task data object groups indicative of tasks to be performed on or by the first reagent component can be represented as GUI element by highlighting the area of the schematic analyzer diagram representing the first reagent component. As a result, the highlighted area of the schematic analyzer diagram can provide a user with an aggregated view on tasks which may need to be performed on or by the highlighted first reagent component of the analyzer.

The aggregated data value of each aggregated task data object group can be used for specifying the GUI element representing the aggregated task data object group. Using the aggregated data value for specifying a GUI element can, but does not necessarily have to, imply displaying an aggregated numerical data value, for example, the total number of tasks indicated by all task data objects belonging to the aggregated task data object group. Likewise, the value of the aggregated data value can be used to specify a GUI element having a particular design, for example, by using different colors or images. For example, providing an aggregated view of a large number of tasks can comprise displaying GUI elements of a different color compared to providing an aggregated view of a small number of tasks. Likewise, providing an aggregated view of a set of highly urgent tasks can involve the specification of GUI elements having a different visual representation (for example, color or icon) than the GUI elements representing routine tasks with low priority.

A value range can comprise a range of user-IDs, a range of device-IDs and the like. Likewise, the position of a lab device can be encoded such that the position-ID of the device comprises both an indicator of the building, of the department and/or the room the device is located in, thereby enabling a coarse-grained or a fine-grained aggregation of task data objects based on an assigned position-ID.

Aggregating data contained in a multitude of task data objects can assist a user in performing tasks more efficiently. In a further advantageous aspect, embodiments used as a laboratory workflow management system can reduce the time to learn because the user does not have to look for and remember which screen to access in order to perform a particular task.

According to further embodiments, a hierarchical drill-down graph comprising at least two hierarchical levels and comprising one or more first nodes can be used for executing the data aggregation. Each first node can have assigned a node attribute. Each received task data object can be represented as a second node of the hierarchical drill-down graph. One of the first nodes can be determined as current node of the hierarchical drill-down graph. The current node can be a starting point for executing a drill-down analysis. The drill-down analysis can be a data aggregation operation executed on the current node and all direct and indirect successor nodes of the current node. When executing the aggregation operation on the nodes, the node attribute of the current node can be used in the aggregation operation as aggregation attribute. For the aggregated task data object group represented by the current node, an aggregated data value can be calculated by executing a data aggregation function over all task data objects represented by any of the successor nodes of the current node.

According to some embodiments, the first nodes of the drill-down graph can specify a predefined graph topology providing for a 'backbone' graph data structure to which a plurality of second nodes respectively representing a task data object can be assigned.

According to further embodiments, the steps of aggregating task data objects can be performed on multiple hierarchical levels of a drill-down graph by selecting a particular node in the drill-down graph. These embodiments can be advantageous, as they can provide a user with multiple levels of data aggregation and with a method to specify for which node, including its direct and indirect successor nodes, a drill-down analysis can be executed.

A drill-down graph can be a data structure comprising data objects represented as nodes and edges of a graph. A drill-down graph can allow the execution of a drill-down analysis of the data contained in its nodes. The pathways to be used in the drill-down analysis can be specified by the drill-down graph's edges.

According to some embodiments, the drill-down graph can comprise a first set of nodes which do not represent task data objects. Each of the received task data object can be represented as node and added to the drill-down graph by creating new edges. The new edges can connect at least some of the first nodes with the newly created nodes representing the received task data objects.

According to some embodiments, all task data objects can be represented as leaf nodes of the drill-down graph. According to further embodiments, at least some of the received task data objects can be represented as non-leave nodes. Depending on the embodiment, the hierarchical drill-down graph can comprise two or more hierarchical levels. Each node of the drill-down graph not being a leaf node can comprise one or more child nodes. At least some nodes in the drill-down graph can be used as starting point for executing a drill-down analysis. The drill-down analysis can be a data aggregation operation executed upon selection of a node as starting node for the drill-down analysis. The node can be referred to as "current node." The data contained in the current node and in its direct and indirect successor nodes can be aggregated during the drill-down analysis. A 'direct successor node' of a node X can be a child node of the node X. An 'indirect successor node' can be any node S that can be reached starting from the node X by traversing the graph downwards, wherein S is not a child node of node X.

According to some embodiments, a drill-down analysis executed for a particular current node can comprise aggregating all task data objects represented by the current node or by a direct or indirect successor node of the current node into aggregated task data object groups. All task data objects belonging to the same aggregated task data object group can share an attribute value or value range of the at least one attribute. The at least one shared attribute value or value range can be indicative of at least one shared step of the task of the attribute's task data object. The shared step can be shared by all tasks of the task data objects of the aggregated task data object group. The specified aggregation GUI elements can be displayed on a graphical user interface for providing the aggregated view.

According to some embodiments, different kinds of attributes can be used in different hierarchical levels of the drill-down analysis. For example, the attribute used for aggregating task data objects of a first level of the drill-down graph may be a room-ID shared by a plurality of lab devices. On a second level of the drill-down graph hierarchy, the attribute used for aggregating groups of task data objects may be a device-ID.

According to further embodiments, a predefined drill-down graph topology can specify the one or more attributes used in each respective drill-down step. This may be advantageous, because the predefined topology can determine which kind of attribute or attributes can be used in each drill-down operation for executing the aggregation step. Other attributes may be ignored thereby saving processing power.

According to further embodiments, at least one navigation GUI element can be displayed. The at least one navigation GUI element can be a selectable pointer to a node of the drill-down graph. Upon selection of the at least one navigation GUI element by a user, the node being pointed at can be used by the selected navigation GUI element as current node. The at least one navigation GUI element can provide a user with the option to specify the starting point for executing a drill-down analysis. The execution of a drill-down analysis can be triggered for the used current node. As a result, the user can be provided an aggregated view on data contained in task data objects which can be represented as direct or indirect successor nodes of the current node used in the drill-down analysis.

According to some embodiments, a 'navigation GUI element' can be any kind of selectable GUI element, for example, a button, an icon or the like.

According to further embodiments, two or more navigation GUI elements can be displayed on the GUI. The displayed navigation GUI elements can constitute a navigation path. The navigation GUI elements of the navigation path connecting nodes can already be used as current node in a drill-down analysis. The navigation path can allow a user to navigate back and forward between nodes of the drill-down graph by selecting navigation GUI elements pointing to the nodes. The last navigation GUI element in the navigation path can be a pointer to a node having been used as current node for executing a drill-down analysis whose resulting aggregated view can be currently displayed. According to embodiments, the first navigation GUI element of the navigation path can point to the root node of the drill-down graph.

According to further embodiments, for each drill-down analysis, at least the aggregated data values can be stored in a drill-down history. The drill-down history can be stored in a working memory. A navigation GUI element can be selected by a user, the user thereby selecting a new current node. The new current node can correspond to a previously executed drill-down analysis. According to some embodiments, the stored aggregated data values aggregated in the previously executed drill-down analysis can be loaded instead of re-executing the drill-down analysis for the selected current node. These features may be advantageous; as aggregated data values having already been calculated in a previous data aggregation step may not have to be re-calculated but can rather be loaded from memory.

A drill-down history can be a data structure stored in the working memory of a computer executing the drill-down analysis. By using the drill-down history, moving forward and backward in the navigation path can be significantly accelerated as memory access times of working memories can be typically very short and a re-calculation of the drill-down analysis can be avoided by making use of previously calculated results.

According to further embodiments, one or more categories can be specified. Each of the one or more categories can be represented as a selectable category GUI element. The selectable category GUI element can be in particular a tab but can also be a button, an icon or the like. For each category, a corresponding drill-down graph can be created. Each of the one or more nodes representing a received task data object can be added to each of the created one or more drill-down graphs. Upon selection of one of the one or more category GUI elements by a user, the drill-down graph can be selected corresponding to the selected category GUI element. A drill-down analysis can be executed. The aggregation step can be executed according to the graph topology of the selected drill-down graph.

The term "category" as used herein can refer to an information architecture providing a particular view on the data contained in the received task data objects. Each category can correspond to a drill-down graph. Depending on the embodiment, the topology of each drill-down graph corresponding to a particular category may be unique, thereby providing a unique graph topology for aggregating and interpreting data contained in the received task data objects.

Using multiple different categories corresponding to multiple different drill-down graphs can be particularly advantageous as a user can thereby be provided with different entry points to work on the received task data objects and can be provided with the option to organize and aggregate tasks according to different schemas. According to embodiments, each category can be selected from a group comprising a 'Routine' category, a 'Lab' category and a 'Utility' category.

The 'Routine' category can encompass data being related to one or more biological samples and data related to the production of analytical results and/or data providing a user with the option to monitor and/or control the execution of a laboratory procedure on one or more biological sample.

The 'Lab' category can be used to organize data according to one or more lab devices existing in a laboratory. Views provided according to the 'Lab' category can provide a user with the option to monitor and/or control the status of one or more lab devices, consumables, and/or waste. For example, the filling level of a reagent, error states of a lab device, or the like can be monitored and the affected device can be started or stopped by the user accordingly.

The 'Utility' category can comprise configuration data which can be used for configuring lab devices, user-roles or user-permissions. The configuration data can also comprise configuration data for one or more tests to be performed on one or more samples, user management related configuration data and/or log entries.

According to further embodiments, one link can be created. The at least one link can connect a first node with a second node. The first node can belong to a first drill-down graph. The first drill-down graph can correspond to a first category. The second node can belong to the first drill-down graph or to a second drill-down graph. The second drill-down graph can correspond to a second category. In the case the second node belongs to the second drill-down graph, the link can connect the first and the second drill-down graph and can provide a user with the option to navigate between drill-down graphs of different categories.

According to some embodiments, the links can be specified by a business analyst, not by an end-user. The usage of links to connect nodes can be particular advantageous for the following reasons:
  unlike edges, a link can connect nodes belonging to different drill-down graphs, thereby allowing the user to navigate between different drill-down graphs.
  if a user wants to change context, for example, wants to view data of one or more groups of task data objects created by aggregating the task data objects according to different drill-down graphs, a link can allow a user to switch between different aggregated views, each aggregated view generated based on the topology of a different drill-down graph.
  a link can allow connecting nodes belonging to distant hierarchical levels separated from each other by one or more other hierarchical levels, thereby allowing a user to skip executing drill-down analyses for each intermediate hierarchical level.
  a link, which is not an edge of one of the drill-down graphs, can allow the introduction of circular navigation paths. As a result, a user can be provided with almost unlimited freedom of navigation within or between multiple drill-down graphs while at the same time the generation of cyclic pathways in the drill-down graph which may lead to inconsistencies is prohibited: the topology of a drill-down graph can be constituted solely by its nodes and edges, not by the links.

According to further embodiments, one or more user-IDs and/or role-IDs can be assigned to each of the received task data objects. The term 'ID' and 'identifier' can herein be used synonymously. A user-ID and/or role-ID of a user can be received upon a login of the user. Upon receipt of the user-ID and/or role-ID, only task data objects can be used for executing a drill-down analysis which can have been assigned the received user-ID and/or role-ID.

In one embodiment, a mobile device can be used for the user identification as the mobile device typically signals the user's telephone number when a communication channel is established between mobile device and server computer which can be used for the user's identification. Each user can be assigned a user-ID which can be an identifier being unique for the user. A user may have assigned a role-ID in addition or instead of a user-ID. A role ID can be a unique identifier for a group of one or more users fulfilling a particular role in a laboratory and having assigned role specific rights and duties. Depending on the embodiment, the user can log into the analysis system via a man-machine interface provided by the server computer, provided by a lab device connected to the server computer and/or provided by any other computer or a mobile device connected to the server computer via a network. The log-in action may be a log-in action into a software system being interoperable with the analysis system, for example, a LIS or a middleware component operable to exchange data with the analysis system.

Upon a login-event received from the server computer, an aggregated view can be provided to the user. The aggregated view can be created by selectively using only task data objects in the aggregation step which have assigned the user-ID and/or role-ID of the user received upon the log-in event. According to some embodiments, the GUI cannot display to the logged-in user any tasks he has no permission to execute. This feature may be advantageous as it can reduce the 'visual noise' presented to a user.

According to further embodiments, one or more user-IDs and/or role-IDs can be assigned to each of the received task data objects. A user-ID and/or role-ID of a user can be received upon a login of the user. The received task data objects can be grouped in dependence on their respectively assigned user-ID and/or role-ID. Only task data objects for executing the aggregation step can be selectively used which have assigned the received user-ID and/or role-ID.

According to further embodiments, each task data object can be assigned an urgency level attribute. Some of the embodiments can further comprise aggregating task data objects according to the value of the assigned urgency level attribute. In the aggregation step, each aggregated task data object group can be assigned an aggregated urgency level value. The aggregated urgency level value can be calculated as the maximum urgency level attribute value of any of the task data objects within the aggregated task data object group. Only GUI elements of those groups of task data objects can be displayed whose aggregated urgency level value is above a threshold. According to embodiments, the steps can be executed after having determined that no-user is logged-in, thereby ensuring that even in the case no user is logged-in an aggregated view on the most urgent tasks to be executed in order to preserve the operability of the analysis system can be provided.

According to embodiments, a task data object representing a completed task can be automatically, or upon a user action, flagged as 'completed'. A task data object comprising the flag cannot be used when executing the aggregation step, thereby further reducing the visual noise.

According to further embodiments, a favorite GUI element can be specified. The favorite GUI element can be a user-specific, selectable pointer to a node within the drill-down graph. The specified GUI element can be displayed. Upon selection of the favorite GUI element, the execution of a drill-down analysis can be executed. In the execution, the node pointed at by the favorite GUI element can be used as current node. A 'favorite GUI element' can be, for example, a selectable button, icon or any other selectable GUI element which can be displayed on a graphical user interface. Favorite GUI elements can allow users to navigate directly to a certain node in a drill-down graph in order to obtain an aggregated view of task data objects according to a drill-down analysis based on using the node as current node.

According to further embodiments, the task data objects of the selected aggregated task data object group can respectively represent a task of inspecting and/or validating a measurement result. Each measurement result can be an analysis result or a calibration result. An analysis result can be generated by analyzing biological samples. A calibration result can be generated by analyzing a calibration sample. Providing the user access to program instructions for executing the step shared by all the tasks can comprise displaying a workflow-execution view. The workflow execution view can comprise one or more task execution GUI elements enabling the user to inspect and/or validate the measurement results. The shared step of the selected aggregated task data object group can be automatically selecting the workflow execution view from a plurality of workflow execution views for display.

For example, a measurement result can be an analysis result generated by the at least one lab device by processing one or more biological samples. According to other examples, each measurement result may be a calibration result generated by a calibrator by processing a calibration sample. The calibrator can be one of the lab devices.

According to embodiments, via the workflow execution view, a confirmation signal indicative of an approval of one of the measurement results by the user can be received. In the case of having received the confirmation signal, the result can be automatically forwarded or made available to the LIS or the middleware of the laboratory.

According to embodiments, the at least one lab device can be one of a plurality of lab devices and the task data objects of the selected aggregated task data object group respectively represent a task of maintaining one of the plurality of lab devices. Providing the user access to program instructions for executing the step shared by all the tasks can comprise displaying a workflow-execution view. The workflow execution view can comprise one or more task execution GUI elements. Each task execution GUI element can comprise information on a current state of one of the lab devices and/or information on how to inspect or repair the lab device.

According to further embodiments, the shared step of the selected aggregated task data object group can be selected from the group comprising:
  executing the maintenance tasks at a shared location, the shared location shared by all lab devices whose maintenance tasks can be aggregated within the selected aggregated task data object group; for example, the shared location may be indicated by a room-ID, department-ID or lab-ID of the room, department or lab where the respective lab device is located;
  selecting the workflow execution view from a plurality of workflow execution views for display; for example, there may be different views specified in an application program, each view comprising a different layout and a different set of GUI elements for executing some maintenance tasks; and
  retrieving one or more consumables from a shared location for making the respective lab device operative, the shared location shared by all lab devices whose maintenance tasks can be aggregated within the selected aggregated task data object group.

According to further embodiments, the shared location can be a particular location comprising consumables which may need to be retrieved from the location, for example, a room, a freezer or other storage facility, to replenish empty consumables of a plurality of lab devices. For example, the shared location may be indicated by a room-ID, or freezer-ID, where the respective consumables can be stored. A workflow execution view can be selected from a plurality of workflow execution views for display. The workflow execution view can comprise a list of consumables to be retrieved from the shared location.

According to embodiments, there may be a first workflow execution view comprising GUI elements designed for displaying an error status without providing automatically resolution to the problem and there may be second workflow execution views comprising GUI elements enabling the user to manipulate the respective lab device. Thus, by aggregating all task data objects sharing the display of a particular workflow execution view, a user can be empowered to solve multiple maintenance tasks at multiple lab devices from one single view without having to switch and navigate between different workflow execution views.

According to embodiments, via the workflow execution view, a confirmation signal indicative of a successful maintenance by the user can be received. In the case the confirmation signal was received, a command can be automatically sent to each of the lab devices for which the confirmation signal was received, thereby automatically activating the lab device and enabling the lab device to execute its respective laboratory procedure.

These features may be advantageous, because the user, maintaining a plurality of lab devices via one and the same workflow execution view can be, in addition, enabled to re-activate each repaired lab device, for example, by clicking on a GUI element of the workflow execution view. In the case the tasks would not have been aggregated in dependence on the shared workflow execution view but rather, for example, chronological, the user may possibly have to switch between multiple different views for maintaining different types of lab devices, making the interaction between man and machine much more efficient.

For example, a plurality of task data objects may be aggregated according to a shared physical location, for example, a room comprising a variety of consumables of various lab devices. A first aggregation GUI element may represent a plurality of tasks for refilling cuvettes, refilling a particular reagent and refilling pipettes, the task can be aggregated based on a shared task step of retrieving the consumables from a particular storage room. The storage room may be represented within the analysis system as an 'unconnected lab device'. A user clicking on the corresponding aggregation GUI element can trigger the display of a workflow execution view comprising a "shopping list." This list can comprise all items to be retrieved from the particular room. According to some embodiments, a background process can monitor the status of the lab devices for calculating a statistical result. The statistical result can be indicative of the average time period until a particular consumable needs to be refilled. This information can be used to automatically create a task data object specifying the task of refilling the corresponding consumable within a predefined security time span before the consumable may be empty. Thus, some embodiments may not only be able to automatically create task data objects in dependence on received status messages of each of the lab devices. Rather, the embodiments can, in addition, be able to automatically create task data objects in advance based on automatically gathered, statistical data. The feature may further improve the efficiency of task aggregation, because items can be added to the shopping list which may not yet empty but may probably have to be refilled soon.

According to further embodiments, the at least one lab device can be one of a plurality of lab devices and the task data objects of the selected aggregated task data object group can respectively represent a task of transporting one or more of the biological samples processed by one of the lab devices specified in the task data objects of the aggregated task data object group from any of the lab devices to a destination location. The destination location can be, for example, a storage unit, a freezer, a fridge, a post-analytical device or the like. The shared step of the selected aggregated task data object group can be transporting one or more of the biological samples to a shared destination location. Providing the user access to program instructions for executing the shared step can comprise displaying a workflow-execution view. Upon receiving, via the workflow execution view, a confirmation signal indicative of a confirmation for the destination location by the user, a signal triggering one or more robotic units to automatically execute the transportation tasks of the selected aggregated task data object group can be automatically submitted to the robotic units. As a consequence, the robotic units, for example, a conveyor belt and/or a robotic arm can automatically transport each of the biological samples processed by any of the lab devices to the shared destination location. This may be advantageous, because where the lab devices are part of an automated, multi-device workcell system, the samples can be collected from multiple lab devices for a collective transport to the destination location.

According to further embodiments, each of the aggregation GUI elements according to a first aggregation GUI element version can be provided. Each GUI element version can correspond to a particular graphical design. The first GUI element version can be displayed on a small screen, such as, for example, a screen of a mobile user device. Each GUI element can be a pointer to one of the first nodes in the drill-down graph. The aggregated view comprising the aggregation GUI elements in a first pane can be displayed. The first pane can be approximately screen size. A second pane approximately screen size can be displayed. The second pane can replace the first pane. The second pane can comprise one or more further aggregation GUI elements, or can comprise one or more task GUI elements. Each task GUI element can represent a task data object of an aggregated task data object group represented by one of the aggregation GUI elements of the first pane. Upon selection of any of the task GUI elements, instructions for executing the shared step of the one aggregated task data object group can be executed.

A GUI element version corresponding to a particular graphical design can be a specification of the size, shape and other features determining the appearance and dynamic behavior of a GUI element on a graphical user interface.

These embodiments can be advantageous as they can provide an aggregated view of data which can be particularly adapted to be displayed on a small screen, for example, of a mobile device of a user such as a smart phone. Some of the embodiments can be used as emergency systems allowing the notification of a user with appropriate permissions and skills, for example, a lab technician, whenever a highly urgent tasks needs to be executed immediately in order to preserve the operability of an analysis system.

According to further embodiments, the content of the second pane can be constructed by selection of one of the aggregation GUI elements in the first pane, selecting one of the first nodes of the drill-down graph as current node. A drill-down analysis can be executed. The drill-down analysis can be a data aggregation operation executed on the current node and all direct and indirect successor nodes of the current node. When executing the aggregation operation on the nodes, the node attribute of the current node can be used in the aggregation operation as aggregation attribute. One or more further aggregation task data object groups can be created. Each of the further aggregated task data object groups can be represented by a further aggregation GUI elements.

This may be advantageous, because the user can be empowered, by selecting one of the first aggregation GUI elements, to execute a drill-down analysis and can receive as a result one or more further aggregation GUI elements which may represent a plurality of task data objects aggregated for one of the child nodes of the node corresponding to the selected first aggregation GUI element. In the case where it is not possible to further drill-down into the graph because bottom of the tree hierarchy is reached, the single task data objects may be represented and displayed as selectable task GUI elements on the second pane. Upon selection of the task GUI element by the user, no further drill-down can be executed, but rather, the execution of instructions for executing the task represented by the selected task data object can be triggered.

According to embodiments, the server computer can continuously monitor status information of the lab devices belonging to an analysis system. Depending on the status information, one or more task data objects can be created and received by the server computer. The aggregating task data objects can be performed by using at least an urgency level attribute assigned to each of the received task data objects as attribute for the aggregation step. In case the aggregated urgency level value assigned to any of the groups of task data objects exceeds a threshold value, one or more users can be notified of the urgent tasks. The notification can be executed by the server computer sending a specification of an aggregated view on the urgent tasks to the mobile device of a user. The user can be a default user, for example, the responsible lab technician. The user can according to further embodiments likewise be a user who can be identified by a user-ID. The user-ID can be assigned to each of the aggregated task data objects.

Since the size of a mobile device is usually small, it can be advantageous to display the results of a drill-down analysis according to a first display mode. The first display mode can be panes approximately screen size. The first display mode can use GUI elements corresponding to a first version of GUI elements. The display mode can also be considered as "full screen mode."

A drill-down analysis can be executed upon selecting a GUI element of the first pane. The aggregated data obtained as a result of the drill-down analysis can be displayed on a second pane. The first pane and the second pane cannot be viewed by the user at the same time. Rather, the second pane can replace the first pane.

As the size of screens used in current computer systems and/or current analysis systems can usually be large enough to allow the simultaneous display of multiple GUI elements at the same time without confusing the user, it can be advantageous to display the results of a drill-down analysis on the graphical user interfaces according to a second display mode. The second display mode can use pane approximately half screen size. The display mode can also be considered as "detailed display mode." GUI elements belonging to a second version of GUI elements can be appropriately sized to be displayed on a medium sized screen such as a screen of a computer system. A drill-down analysis can be executed upon selecting a GUI element of the first pane. The aggregated data obtained as a result of the drill-down analysis can be displayed on a second pane. The first pane and the second pane can be viewed by the user according to the second display mode at the same time.

According to further embodiments, each of the GUI elements can be provided according to a second GUI element version. A GUI element version can correspond to a particular graphical design. The second GUI element version can be displayed on a medium-sized screen, such as, a screen of a computer system or a screen of a lab device. Each GUI element can be a pointer to a node in the drill-down graph. First GUI elements can be displayed in a first pane. The first pane can be approximately half screen size. Upon selection of first GUI elements, using the node pointed at by the selected GUI element can be used as current node and executing a drill-down analysis. The GUI elements displayed can be second GUI elements. The second GUI elements can be displayed in a second pane. The second pane can be approximately half screen size. The first pane and the second pane can be displayed at the same time.

According to further embodiments, embodiments providing an aggregated view can be implemented by an analysis system for analyzing biological samples. The analysis system can comprise one or more lab devices. According to further embodiments, a user can be identified by the one or more lab devices. A user identifier of the identified user and a device identifier of the one of the first and second lab devices can be sent to a server computer. A task to be executed by the identified user can be determined by the server computer. The server computer thereby can use the user identifier and the device identifier and can send a signal comprising task data objects indicative of the determined task from the server computer to the lab device.

According to embodiments, an aggregation threshold can be specified, for example, by a business analyst. An aggregation threshold can be the minimum number of task data objects that need to be contained within a task data object group in order to determine an aggregated data value and to use the data value for specifying a GUI element representing an aggregated task data object group. According to the embodiments, the number of task data objects in a current task data object group can be determined. In the case the determined number exceeds the aggregation threshold, a drill-down analysis can be executed and a user can be provided with an aggregated view. In the case where it is determined that the current number of task data objects does not exceed the aggregation threshold, each single task data object can be graphically represented in the form of a separate GUI element.

According to some embodiments, one or more of the GUI elements representing an aggregated task data object group can be link GUI elements displayed in a separate area of the screen which can herein be referred to as "tasks area." Each aggregation element can provide a user with access to program instructions for performing the one or more tasks represented by the aggregation GUI element. For example, if twelve task data objects each indicate the task of manually evaluating the plausibility of a measurement value obtained as analysis result, an aggregation GUI element representing the twelve aggregated task data objects can comprise a link which, when selected, can trigger the display of a more detailed view, the view containing data required for executing the evaluation.

For example, upon selection of the aggregation GUI element, calibration data of the analytical device used for obtaining the measurement values can be displayed. The calibration data can be required for evaluating the plausibility of an obtained measurement value.

According to further embodiments, selecting an aggregation GUI element by a user can trigger the execution of a laboratory procedure on one or more samples by a lab device and/or triggers the display of one or more selectable GUI elements for controlling, for example, starting and/or stopping the lab device.

According to some embodiments, each task data object can comprise at least a first and a second attribute. In the case a first current node is selected, the first attribute can be used for executing a first drill-down analysis. In the case a second current node is selected, the second attribute can be used for executing a second drill-down analysis, the first and the second attribute not being identical.

For example, during the execution of a first drill-down analysis, a room-ID may be used as attribute for aggregating task data objects. In a second drill-down analysis executed for example for a particular group of task data objects all having been assigned to a particular room-ID, a device-ID can be used as attribute for aggregating all task data objects assigned the room-ID. Depending on the embodiment, the attribute or attributes used in the aggregation step may be predefined, specified by a business-analyst and/or specified by an end-user. In addition, one or more grouping steps based, for example, on a user-ID assigned to the task data objects may be executed while executing the drill-down analysis, thereby further reducing the visual noise.

According to some embodiments, the status of the at least one lab device can be monitored by the server computer. The server computer can dynamically create or receive new task data objects and/or can modify or delete at least some of the received task data objects depending on the received status information. Upon creating, modifying or deleting a received task data object, the re-execution of a drill-down analysis can be triggered. As a result of the re-execution, a dynamically updated, aggregated view can be provided to the user.

In accordance with further embodiments, an analysis system for analyzing biological samples can be provided. The analysis system can comprise at least one lab device and a server computer having a server interface component for receiving task data objects. Each task data object can comprise at least one attribute. At least some of the received task data objects can be indicative of a laboratory procedure to be performed by the at least one lab device. The server computer can comprise a processing component for aggregating at least some of the received task data objects into aggregated task data object groups. All task data objects belonging to the same aggregated task data object group can share the same attribute value or attribute value range of the at least one attribute. The at least one shared attribute can be indicative of at least one shared step of the task of the attribute's task data object. The shared step can be shared by all tasks of the task data objects of the aggregated task data object group. A selectable aggregation GUI element can be specified for each of the aggregated task data object groups. The aggregation GUI element can represent the aggregated task data object group. The aggregation GUI elements can be displayed in an aggregated view. Upon selection of an aggregation GUI element by a user, the aggregated task data object group represented by the selected aggregation GUI element can be selected. The user access to program instructions for executing the shared step of the selected aggregated task data object group can automatically be provided.

The server computer system can further comprise a graphical user interface for displaying the specified aggregation GUI elements for providing the aggregated view.

Depending on the embodiment, the graphical user interface can be part of a lab device, can be part of the server computer system, and/or can be part of any other processing device connected to the server computer via a network. The other processing device can be, for example, a mobile device of a user or a computer connected to the intranet of the laboratory.

According to some embodiments, a device-ID can be assigned to at least some of the received task data objects. The device-ID can be indicative of a lab device. At least one lab device belonging to the analysis system can comprise a device identification component for identifying the lab device at the server computer via the lab device's device-ID. According to the embodiments, the server computer can comprise a service interface component. The server interface component can send a signal to the identified lab device. The signal comprising data can be aggregated on all received task data objects to which was assigned the device-ID of the identified lab device. As a result, a user working on the lab device can constantly be kept up to date regarding the tasks that need to be executed in the laboratory, in particular urgent tasks.

According to further embodiments, the device-ID can be indicative of a mobile device of the user. The server computer can identify the mobile device via its device-ID, for example, the mobile number of the user. The server interface component can send a signal to the identified mobile device. The signal can comprise data aggregated on all received task data objects to which was assigned the user-ID of the user of the identified mobile device. As a result, a user can constantly be kept up to date regarding the tasks that need to be executed in the laboratory, in particular urgent tasks, via his mobile device.

According to further embodiments, a user-ID and/or role-ID can be assigned to at least some of the received task data objects. Each user-ID can be indicative of one user. Each role-ID can be indicative of a role assigned to at least one user. The at least one lab device can comprise a user identification component for identifying a user by the user's user-ID and/or role-ID and an interface component for sending the user-ID and/or role-ID of the identified user. The server computer can comprise a service interface component. The server interface component can send a signal to the lab device identified by the device-ID. The signal can comprise data aggregated on received task data objects assigned the user-ID and/or role-ID of a user identified by the lab device. According to further embodiments, the server computer can in addition send the signal to a mobile device of the identified user.

According to further embodiments, the user can identify himself at the server computer via a graphical user interface provided by the server computer. The graphical user interface can be a screen of the server computer or can be a monitor screen of a further computer system. The further computer system can be connected to the server computer via a network, for example, the intranet of a laboratory.

In accordance with some embodiments, an analysis system for analyzing biological samples can be provided comprising a lab device. The lab device can have a user identification component for identifying a user, a device identification component for identifying the lab device, and an interface component for sending a user identifier of the identified user and a device identifier of the lab device, and a server computer having a server interface component for receiving the user identifier and the device identifier, a processing component for determining a task to be executed by the identified user. The server interface component can send a signal to the lab device identified by the device-ID via the service interface component. The signal comprising data aggregated on received task data objects can have assigned the user-ID and/or role-ID of the user identified by the lab device. These embodiments can be advantageous as the user can be informed regarding one or more tasks that need to be executed by that user by the server computer upon logging in using the lab device. This can enable a highly convenient and efficient operation of the analysis system.

In accordance with an embodiment, completion of the execution of a task can be signalled to the server computer. For example, the user can use a lab device for execution of the determined task and then can enter an acknowledgement into the lab device such that completion of the execution can be signalled from the lab device to the server computer. In accordance with an embodiment, the server computer can comprise a database for assigning a first set of tasks to the first lab device and for assigning a second set of tasks to the second lab device. The processing component of the server computer can generate a message when the determined task is not assigned to the identified lab device in the database.

According to further embodiments, a user can be identified by a lab device. A user identifier of the identified user and a device identifier of the lab device can be sent to a server computer. At least one task data object can be determined by the server computer using the user identifier and the device identifier. The at least one task data object can be indicative of the determined task. A signal comprising the task data objects can be sent from the server computer to the one of the lab devices.

In accordance with an embodiment, the mobile device of the analysis system can receive a signal comprising task data objects indicative of the at least one determined task and also indicative of the lab device to be used for execution of this task. In addition, the task data objects can be indicative of the position of the lab device to be used for execution. The position information can comprise an indication of the geographic and/or topological location of the lab device. For example, the position information can be provided as a laboratory room number for indicating the laboratory room in which the lab device can be located.

In accordance with an embodiment, the analysis system can further comprise a mobile device. The mobile device can receive the signal indicative of the determined task. This signal can also be indicative of lab devices used for execution of the determined task. This can be advantageous as the integration of at least one mobile device into the analysis system can allow ubiquitous operation of the analysis system. In accordance with an embodiment, the task data objects contained in the signal received from the server can be indicative of a priority of the tasks. In response to receipt of the signal by the mobile device or the lab device, the tasks can be aggregated and an aggregated urgency level can be calculated for each aggregated task data object group. The aggregated task data objects can be represented by a displayed GUI element only in case the aggregated urgency level of an aggregated task data object group exceeds a threshold value. According to other embodiments, the mobile device upon completion of a determined task can send a message indicating completion of the task to the server computer.

Referring initially to FIG. 1, FIG. 1 is a flowchart of a method providing an aggregated view to a user. In step 251, task data objects can be received, for example, by a server computer. At least some of the received task data objects can be indicative of a laboratory procedure to be performed by the lab device. In step 252, the received task data objects can be aggregated into aggregated task data object groups. All task data objects belonging to the same aggregated task data object group can share the same attribute value or attribute value range of an attribute. The shared attribute can be indicative of a step which can be shared by all tasks represented by the respective task data objects of the aggregated task data object group. In step 253, a selectable aggregation GUI element can be specified for each of the aggregated task data object groups. The aggregation GUI element can be representative of the aggregated task data object group it represents. In step 254, the one or more aggregation GUI elements can be displayed in an aggregation view. Then, in step 255, upon selection of the aggregation GUI elements by a user, the aggregated task data object group represented by the selected aggregation GUI element can be selected. The user can automatically be provided access to program instructions for executing the step shared by all tasks of the task data objects of the selected aggregated task data object group.

Figure 2:
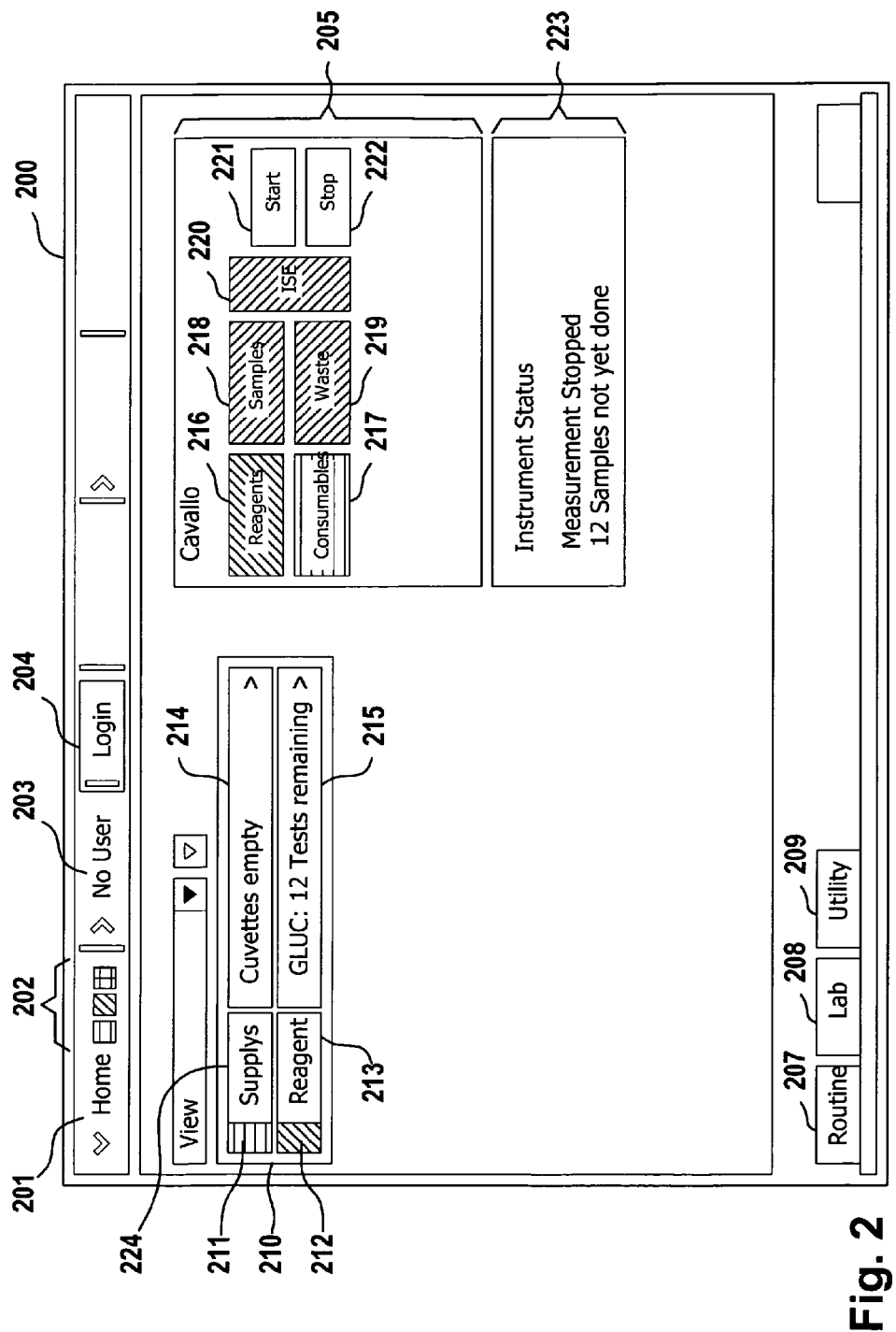
FIG. 2 illustrates a screenshot of a graphical user interface (GUI) when no user is logged in according to an embodiment of the present disclosure.

FIG. 2 depicts a screenshot of a graphical user interface (GUI) when no user is logged in. The GUI element 203 can indicate that currently no user is logged in. The selectable GUI element 204 can trigger, upon selection, the display of a log-in dialog window 300 (see FIG. 3) to the user.

The overview pane 201 can comprise a tasks area 210, a lab device area 205 and a lab device status area 223. Lab device area 205 can display information on the lab device named 'Cavallo' in greater detail. Cavallo can comprise multiple logical, functional and/or physical subunits. A reagents subunit represented by GUI element 216 can comprise one or more reagents for executing a particular analysis. A consumables subunit represented by GUI element 217 can comprise consumables such as disposable cuvettes or pipette tips. A waste subunit can be represented by GUI element 219 and a samples subunit for receiving and/or storing biological samples can be represented by GUI element 218. Selectable GUI elements 221, 222 can be displayed and can allow a user to start or stop the lab device Cavallo.

The GUI elements 221, 222 can allow a user to control the operation of the lab device via the GUI depending on the dynamically displayed status information on the lab device and/or tasks to be performed by the lab device. The lab device status area 223 can provide a user with an aggregated view on tasks to be performed by one or more lab devices or by one or more subunits of a lab device. If one or more tasks needs to be performed by or in respect to one of the subunits, the subunit can be highlighted. In the depicted embodiment, the GUI element 217 representing the "consumables" subunit comprising the empty cuvette container can be assigned a red color. The color can indicate that immediate intervention of a user may be necessary in order to restore or preserve operability of the analysis system. In the case the server computer determines that further tasks need to be performed not immediately but in the near future, the tasks can be indicated by another color, for example, yellow. According to the embodiment depicted in FIG. 2, the reagents subunit can comprise enough reagents for performing the scheduled analyses but may need to be refilled soon. According to embodiments, the discrimination between tasks to be executed immediately and tasks to be executed in the near future can be specified by using threshold values, for example, threshold values for a particular period of time until a consumable may be used up, a particular number of samples which can still be processed given a particular amount of consumables and the like.

Tasks which have to be executed immediately in order to preserve or restore operability of the analysis system can be referred to as "tasks of highest priority." According to one embodiment, the highest priority can be indicated by red color. Tasks which need to be executed soon, but not immediately, can be indicated by a second color, for example, yellow. The second color can represent a second urgency level. Tasks which can be executed by a user at any time can be indicated by a third color, for example, gray or green. The third color can represent the lowest urgency level.

In the depicted embodiment, the one or more tasks to be executed immediately in respect to the consumables subunit can be indicated by displaying a GUI element 217 representing the consumables subunit of "Cavallo" according to the color indicating the highest urgency level. The corresponding one or more tasks 214 displayed in the in the tasks area 210 in the form of an aggregation GUI element can comprise a colored area 211 which can be assigned the color of the highest urgency level. The area 212 in the tasks area 210 and the "reagents" area 216 in the lab device area 205 can be assigned the color representing the second urgency level (yellow).

According to the depicted embodiment, each task depicted in the tasks area 210 can further comprise a text 224, 213 indicating the type of the aggregated tasks, for example, "Supplies" or "Reagent" in case the aggregated task data objects relate to replenishing supplies or refilling reagents.

The tasks area 210 can display data aggregated on one or more tasks. GUI element 214, for example, can be an aggregation GUI element indicating that the cuvette container of the lab device Cavallo is empty and needs to be refilled. Refilling the cuvette container may relate to a single task or a multitude of tasks. For example, if the cuvette container comprises multiple different types of cuvettes which have to be replenished and have to be retrieved from different storage rooms, a multitude of task data objects indicating the tasks can be dynamically specified. GUI 200 can provide the user with an aggregated view on one or more tasks to be executed by or in respect to Cavallo, thereby hiding details such as the type of the cuvettes to be replenished. As a result, the user can be provided with a quickly comprehensible overview on the system state and urgent tasks. The aggregation GUI element 215 can provide an aggregated view on twelve tasks which relate to twelve remaining glucose tests which may not be executed due to the unavailability of cuvettes. The aggregated view on tasks can be highly advantageous, because in the context of a laboratory running large screens a list of tests to be performed on a set of samples may comprise several hundred or thousand items whose display in the form of a non-aggregated task list can disturb the user.

The group of squares 202 can indicate the urgency level of the dynamically specified task data objects. The urgency level of a task data object can represent the priority of the task indicated by the task data object. In the case when one or more tasks having assigned the highest urgency level are received by the server computer, the square at the left side can turn into the color of the highest urgency level, for example, red. In the case when one or more tasks having assigned the second urgency level were determined, the central square can turn into the color of the second urgency level, for example, yellow.

The lab device status area 223 can display information on the current status of the lab device displayed in lab device area 205. Lab device status area 223 in the depicted example can indicate that all measurements were stopped and twelve biological samples may still need to be processed by Cavallo.

Selectable GUI element "Routine" 207 can be a tab element which can represent a first category "Routine" and can provide access to a corresponding drill-down graph. Likewise, selectable GUI elements "Lab" 208 and "Utility" 209 can represent a second and third category. The second category can correspond to a second drill-down graph and the third category can correspond to a third drill-down graph. By selecting one of the selectable category GUI elements 207, 208, 209, a user can specify according to which drill-down graph a drill-down analysis is to be executed. Each task can be indicated by a task data object dynamically received by the server computer.

The overview pane 201, herein also referred to as "home" pane, can display aggregation GUI elements representing aggregated task data objects also in the case where no user is logged into the analysis system. In the case the analysis system comprises multiple lab devices and tasks having assigned a high priority urgency level are assigned to more than one lab device, the lab device area 205 may also display multiple different lab devices. In this case, the whole lab device can be color-encoded according to the urgency level colour schema explained previously. The main function of the overview pane 201 can be to inform a user irrespective of his role and assigned responsibilities on task which have to be immediately executed in order to keep the analysis system running.

Figure 3:
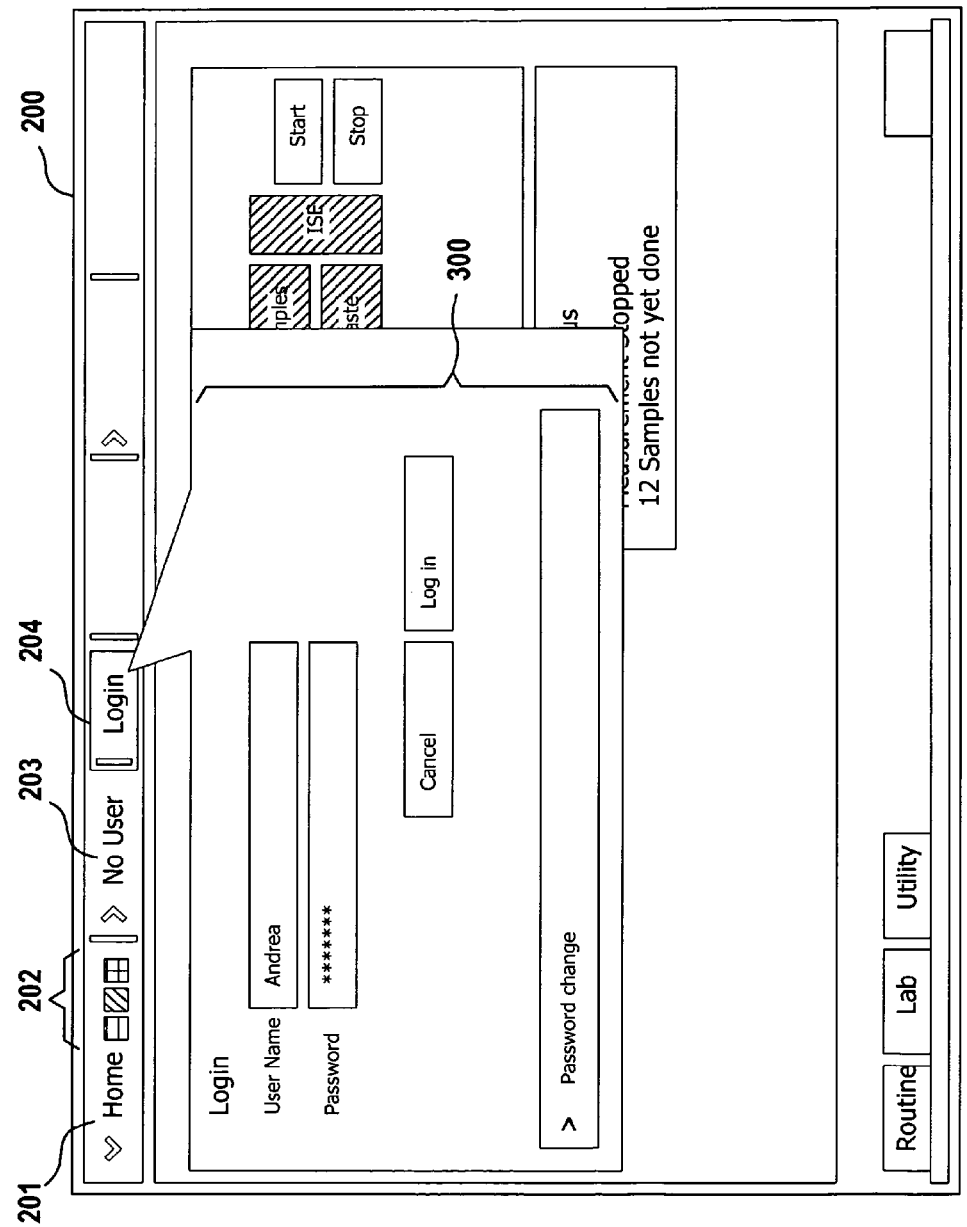
FIG. 3 illustrates a screenshot of a login dialog provided to a user according to an embodiment of the present disclosure.

FIG. 3 is a screenshot of a login dialog provided to a user, for example, upon selecting the login GUI element 204.

Figure 4A:
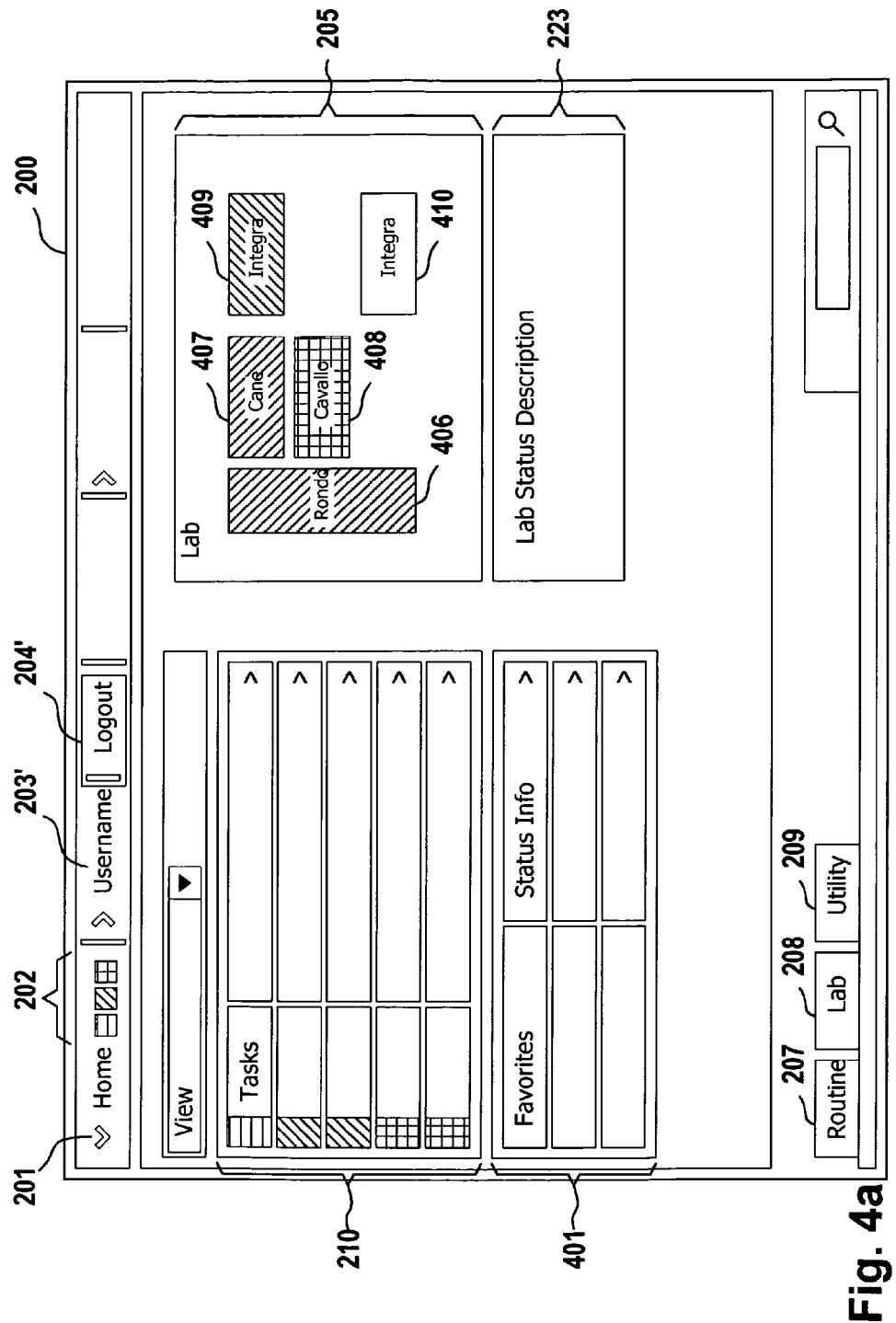
FIG. 4a illustrates a schematic drawing of an overview pane according to an embodiment of the present disclosure.

FIG. 4a is a schematic drawing of an overview pane displayed when a user has successfully logged into the analysis system. The username of the logged-in user can be displayed in GUI element 203'. Upon selection of GUI element 204', the user can log out again. Upon a successful login of a user, the overview pane 201 displayed to a logged-off user as described for FIG. 2 can be complemented with user profile specific information, in particular user-specific tasks and favorites. The favorites pane 401 can be a 2-column table comprising user-defined favorites in the first column and dynamically retrieved status information on each favorite item in the second column. The lab device pane 205 can display a set of GUI elements 406-410 representing lab devices "Rondo", "Cane", "Cavallo", "Integra 1" and "Integra 2." The lab devices can be monitored by the server computer.

Figure 4B:
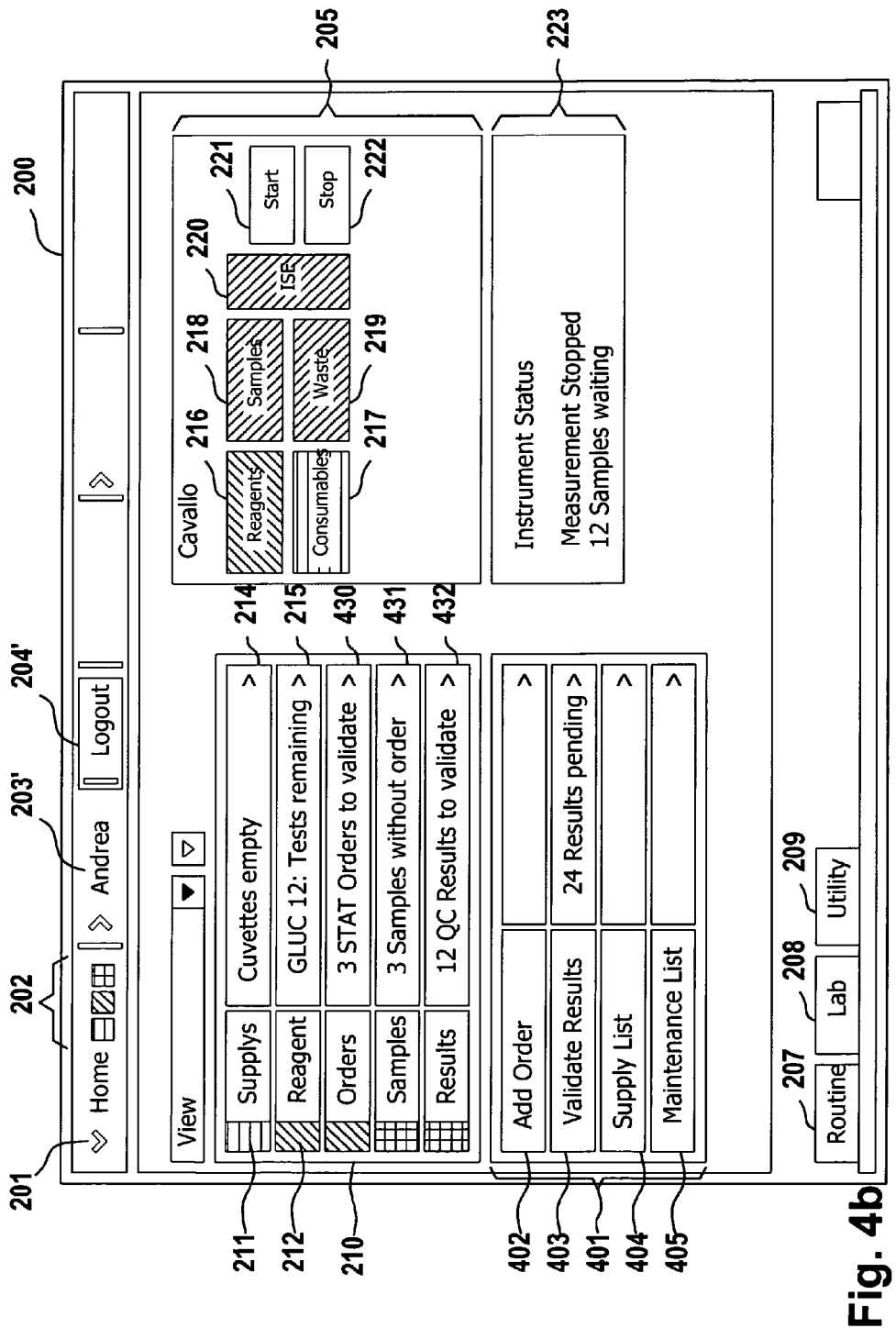
FIG. 4b illustrates the overview pane displaying user specific data according to an embodiment of the present disclosure.

FIG. 4b depicts the overview pane after its complementation with user-specific information. Tasks area 210 can comprise GUI elements 430, 431 and 432, each providing an aggregated view on one or more user specific tasks. The GUI elements can be displayed in addition to the GUI elements 214, 215 providing an aggregated view on one or more tasks assigned a high urgency level. The aggregated view provided to a logged-in user by the tasks area 205 can urge a user to do tasks having a high priority level before performing routine tasks.

The favorites pane 401 can display four favorites GUI elements 402-405 having been specified by the logged-in user. If available, status information for each favorite item can be displayed. Each favorite GUI element can represent a particular node in a drill-down graph, thereby representing also a particular aggregated view of task data objects. Each favorite GUI element 402-405 can be a selectable GUI element allowing a user to navigate to aggregated view of task data objects represented by the selected favorite GUI element. A user can save time by directly selecting favorite GUI element 403 instead of traversing a drill-down graph until a node and a corresponding aggregated view for evaluating analysis results is reached.

Figure 5A:
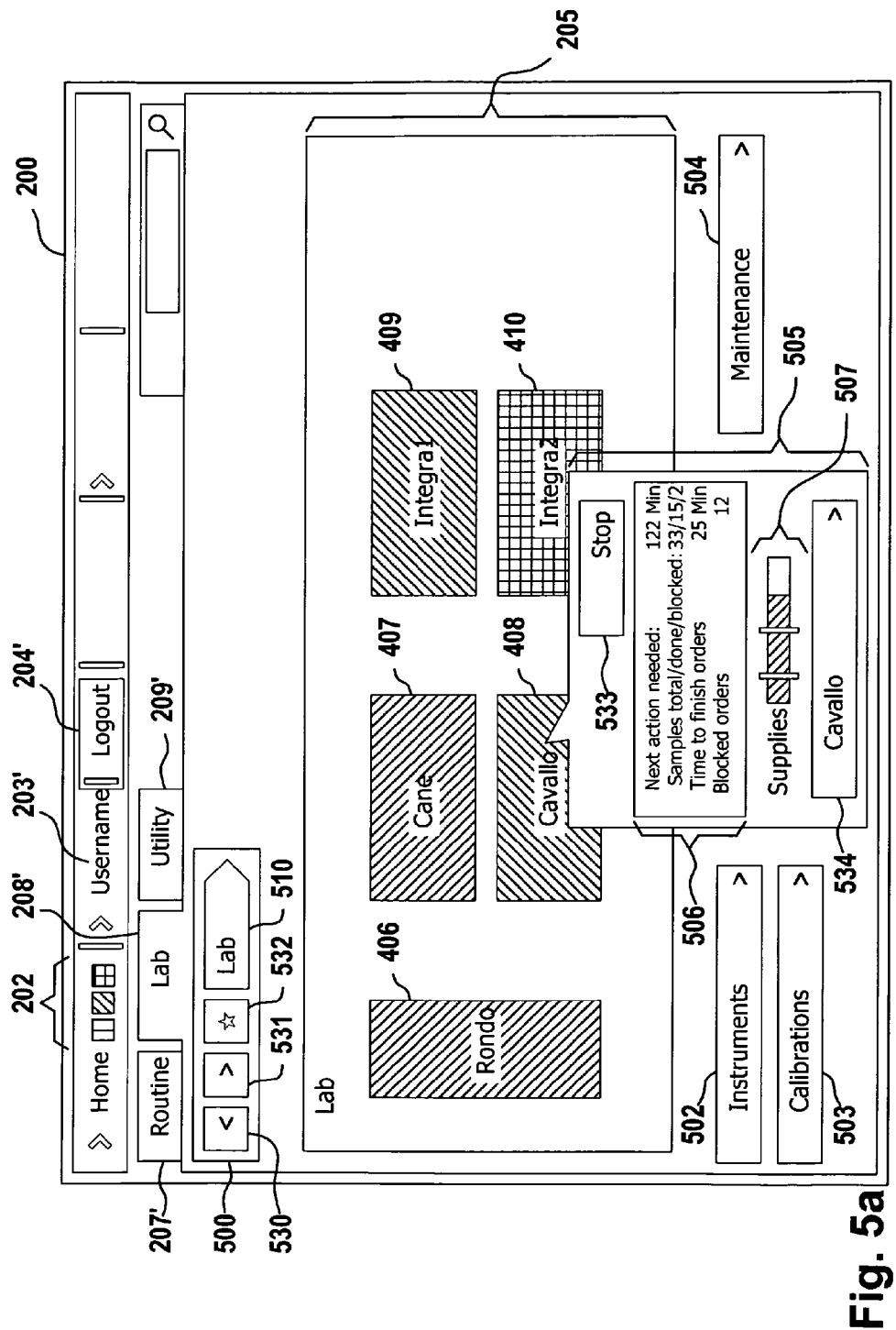
FIG. 5a illustrates an overview on available lab devices displayed upon selection of the 'Lab' category tab according to an embodiment of the present disclosure.
Figure 5B:
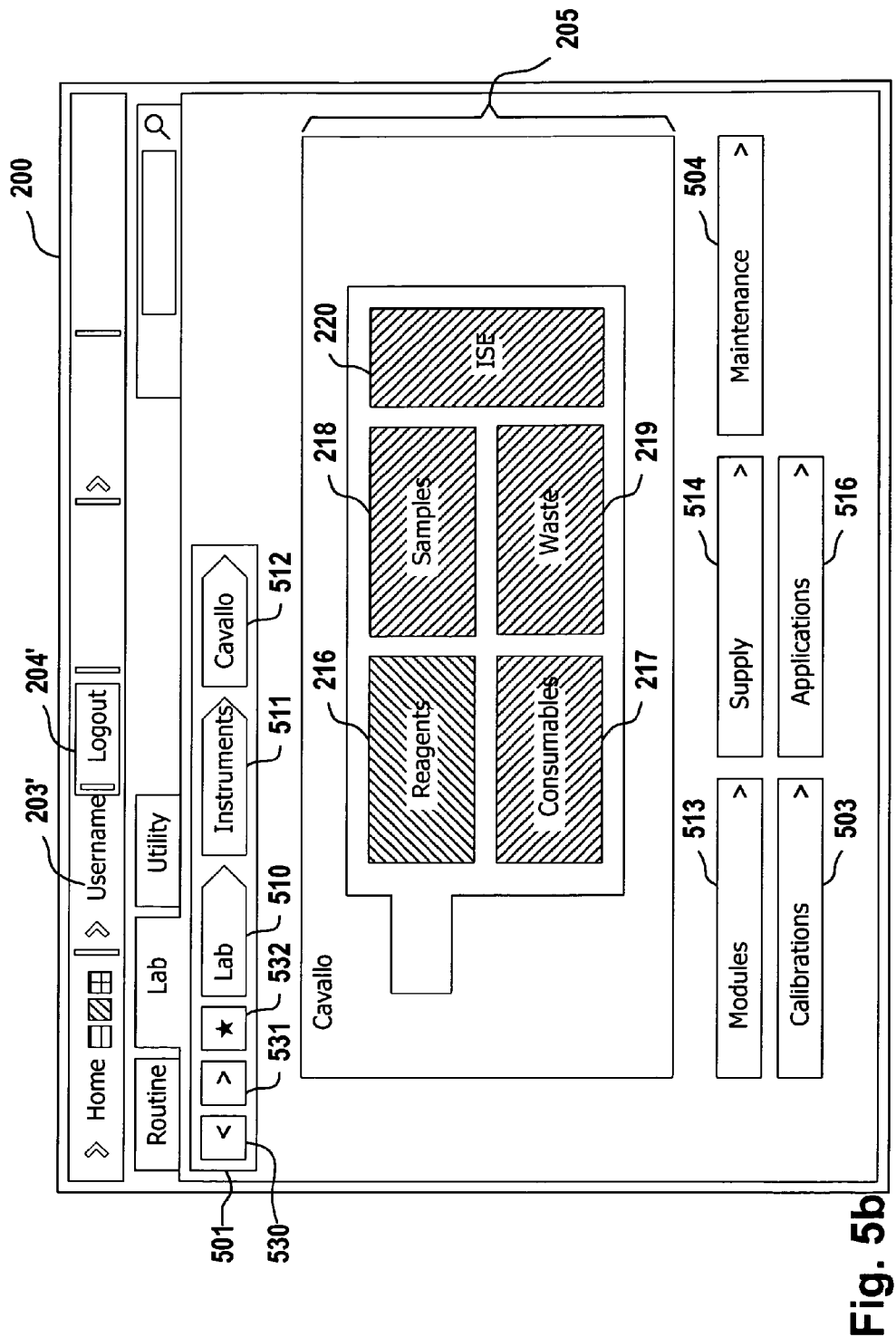
FIG. 5b illustrates an aggregated view on consumables used by the lab device 'Cavallo' according to an embodiment of the present disclosure.

FIGS. 5a and 5b illustrate the execution of a drill-down analysis. FIG. 5a depicts an overview on available lab devices displayed upon selection of the 'Lab' category tab 208'. By selecting the 'Lab' category tab, the user can also select a particular drill-down graph which can be used for executing a drill-down analysis (see FIG. 9, drill-down graph "Lab"). The navigation path 500 can indicate to a user his current position within the drill-down graph. The navigation path 500 can comprise GUI elements. The selectable GUI element 530 can allow a user to navigate "backward" in the chosen navigation path. The selectable GUI element 531 can allow a user to navigate "forward", i.e. downwards in the selected drill-down graph provided the user already visited the selected nodes beforehand. The name of the currently selected node of the drill-down graph can be displayed in a GUI element 510 at the right end of the navigation path 500. In order to allow the user to navigate to nodes the user has not yet visited, additional selectable GUI elements 502, 503, 504 can be displayed which correspond to other nodes of the currently selected drill-down graph. As indicated by GUI element 510 in FIG. 5a, the user currently selected the "Lab" drill-down graph and selected the root node "Lab" as current node.

The selectable GUI element 532 can allow a user to specify new favorites which can be displayed after their specification in favorite area 401.

A user may control the operation of a particular lab device, for example, Cavallo, by selecting a GUI element 408 representing the device with the right mouse button and selecting the "Stop" context menu element 533. The context menu 505 can comprise status information 506 of the selected lab device Cavallo. Upon selecting context menu item 534, a user can select a node in the 'Lab' drill-down graph representing the lab device 'Cavallo' as current node, thereby triggering the execution of a drill-down analysis based on the selected current node 'Cavallo'. As a result, device-component-IDs of logical, functional and/or physical subunits of Cavallo can be used as attribute in the aggregation step executed during the triggered drill-down analysis. Accordingly, all task data objects represented as direct or indirect successor nodes of the selected current node 'Cavallo' and assigned the same device-component-ID or device-component-ID range can be grouped into the same task data object group.

FIG. 5b depicts an aggregated view on consumables, reagents and other items used by the lab device named 'Cavallo', the aggregated view being the result of a drill-down analysis executed for the lab device by selecting the context menu item 534. The navigation path 501 can comprise a set of navigation GUI elements 510, 511, 512 which can specify a path in the drill-down graph starting from the root node "Lab" 510 represented by the tab 208' and ending in the currently selected current node "Cavallo" represented by GUI element 408. The lab device pane 205 can provide the logged-in user with an aggregated view on five groups of tasks which may need to be executed on five logical, functional and/or physical components of Cavallo. In case a user selects a particular lab device, for example, Cavallo, as current node, all task data objects grouped into the same group can share at least a particular device-component-ID as attribute.

The selectable GUI elements 503, 513, 514, 516 displayed to the user can correspond to other nodes of the currently selected drill-down graph. Upon selection by a user, the node represented by the selectable GUI element can be used as new current node.

As a result of selecting the node representing the lab device 'Cavallo' as current node in the 'Lab' drill-down graph, a drill-down analysis can be executed and an aggregated view on task data objects having assigned Cavallo's device-ID can be provided to the user as displayed in FIG. 5b. The attribute used for aggregation the direct and indirect successor nodes of the 'Cavallo' node can be the device-component-ID. As a result of the drill-down analysis, five different groups of task data objects can be created and five GUI elements providing an aggregated view on one or more task data objects can be displayed: "Reagents", "Consumables", "Samples", "Waste", and "ISE". For each of the groups of task data objects, the data contained in the task data objects belonging to the group can be aggregated to generate an aggregated data value. According to the depicted embodiment, the generated data value for each of the five groups can be indicative of whether one or more task data objects representing tasks of the highest or second highest urgency level have been found. In case at least one task data object of a task data object group has assigned a high urgency level value, the color of the aggregation GUI element representing the group can turn into the color representing the urgency level, for example, red for the highest urgency level or yellow for the second highest urgency level.

In FIG. 5a, the GUI element 408 representing Cavallo and the GUI element 409 representing Integral are displayed in yellow color indicated by a particular hachure. The color can indicate to a user that one or more tasks have to be executed on Cavallo and Integral in the near future (yellow can represent the second highest urgency level). By selecting the node representing 'Cavallo' as current node, the user can command the server computer to provide a more detailed view on the tasks to be executed on Cavallo. As a result, a drill-down analysis can be executed for the current node 'Cavallo' and an aggregated view on tasks to be executed in respect to five of Cavallo's logical, functional and/or physical subunits can be provided to the user as shown in FIG. 5b. In FIG. 5b, the reagents subunit GUI element 216 is displayed in yellow color, thereby indicating that one or more tasks have to be executed which can be related to the reagents compartment. By selecting the GUI element 216, the user can trigger the execution of a further drill-down analysis for the reagents subunit of Cavallo. As a result, the user can be provided with a more fine-grained aggregated view on the tasks which have to be performed by or in relation to the reagents subunit (not shown).

Figure 6A:
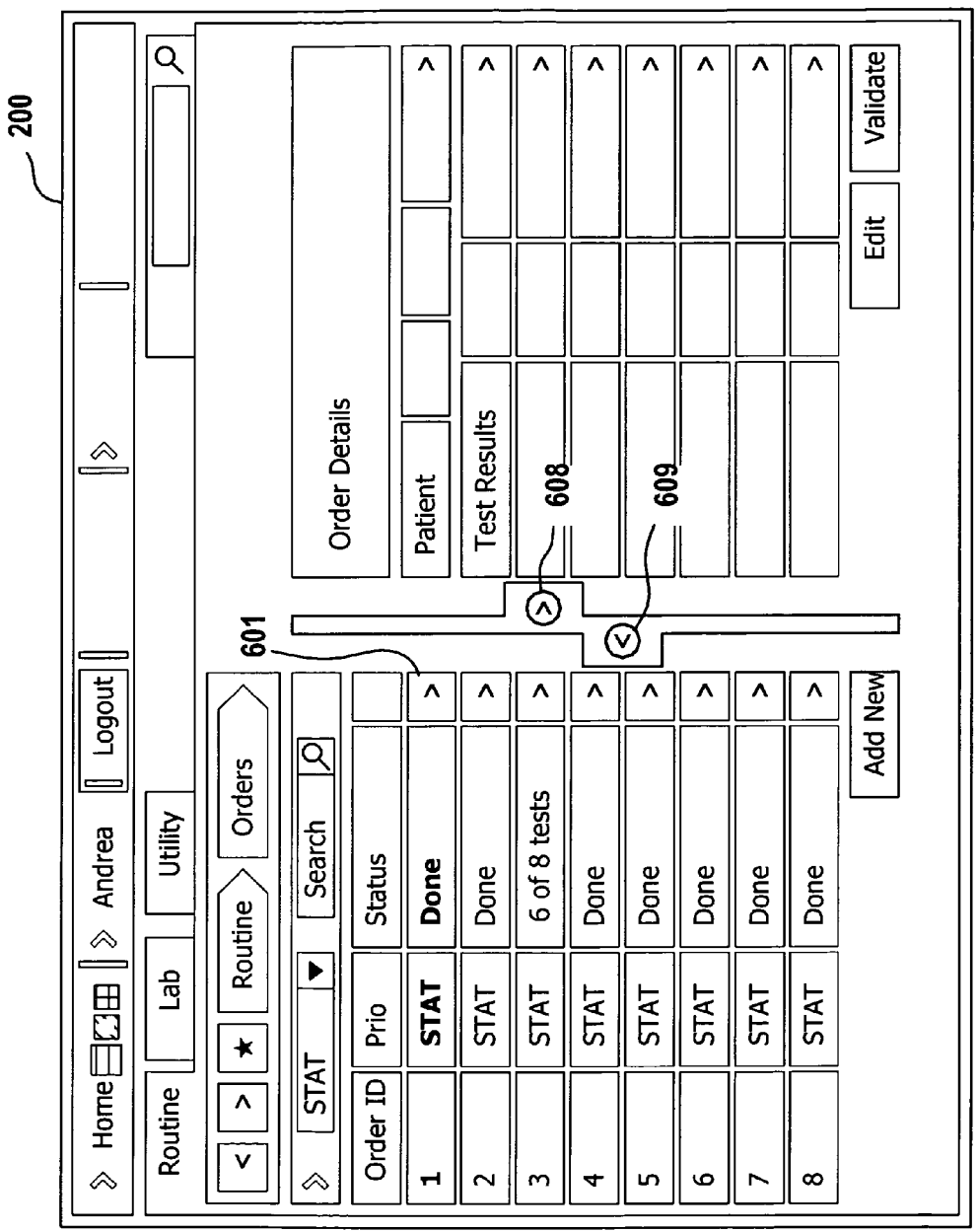
FIGS. 6a-c illustrate the dynamic specification and aggregated display of tasks according to an embodiment of the present disclosure.
Figure 6B:
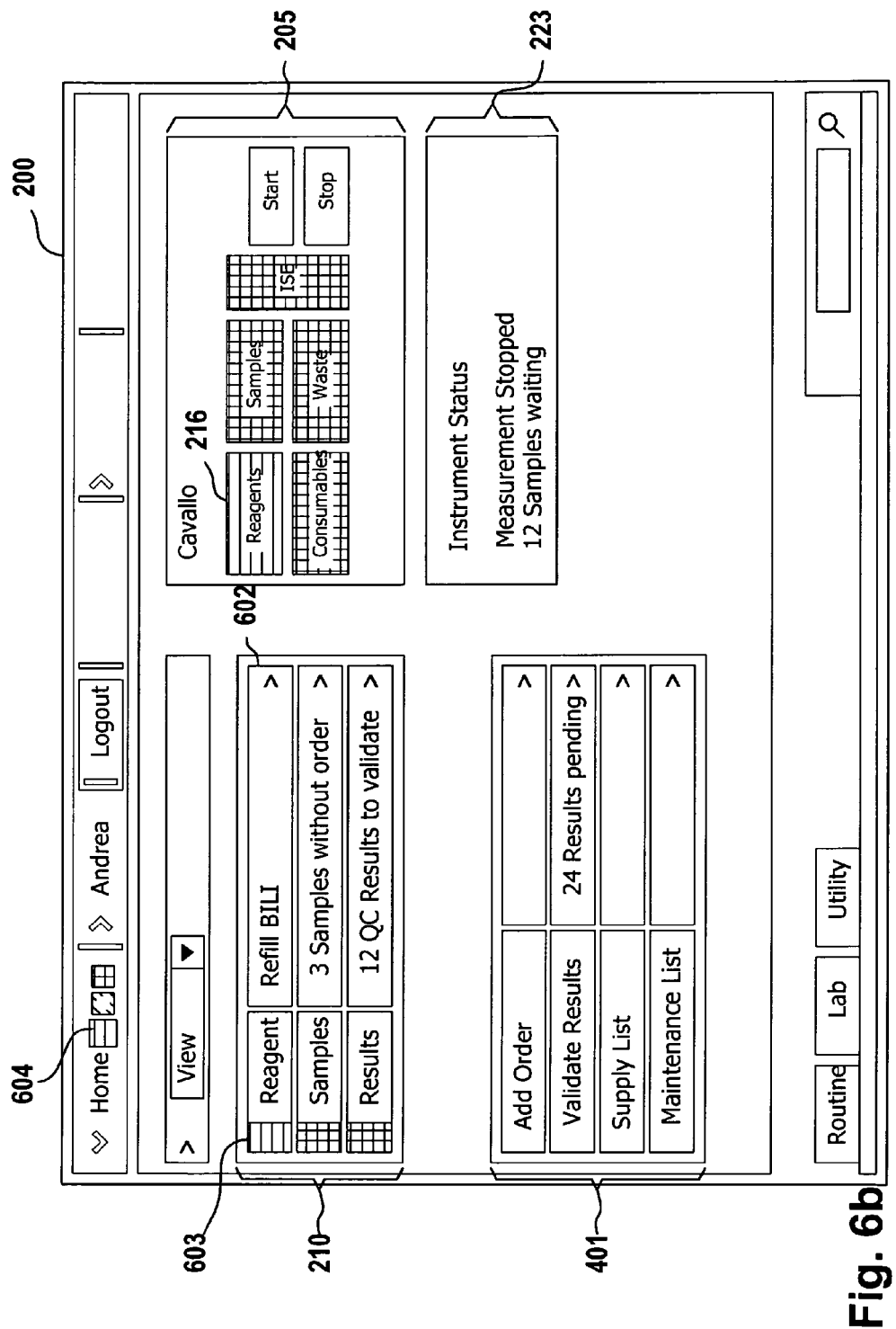
Figure 6C:
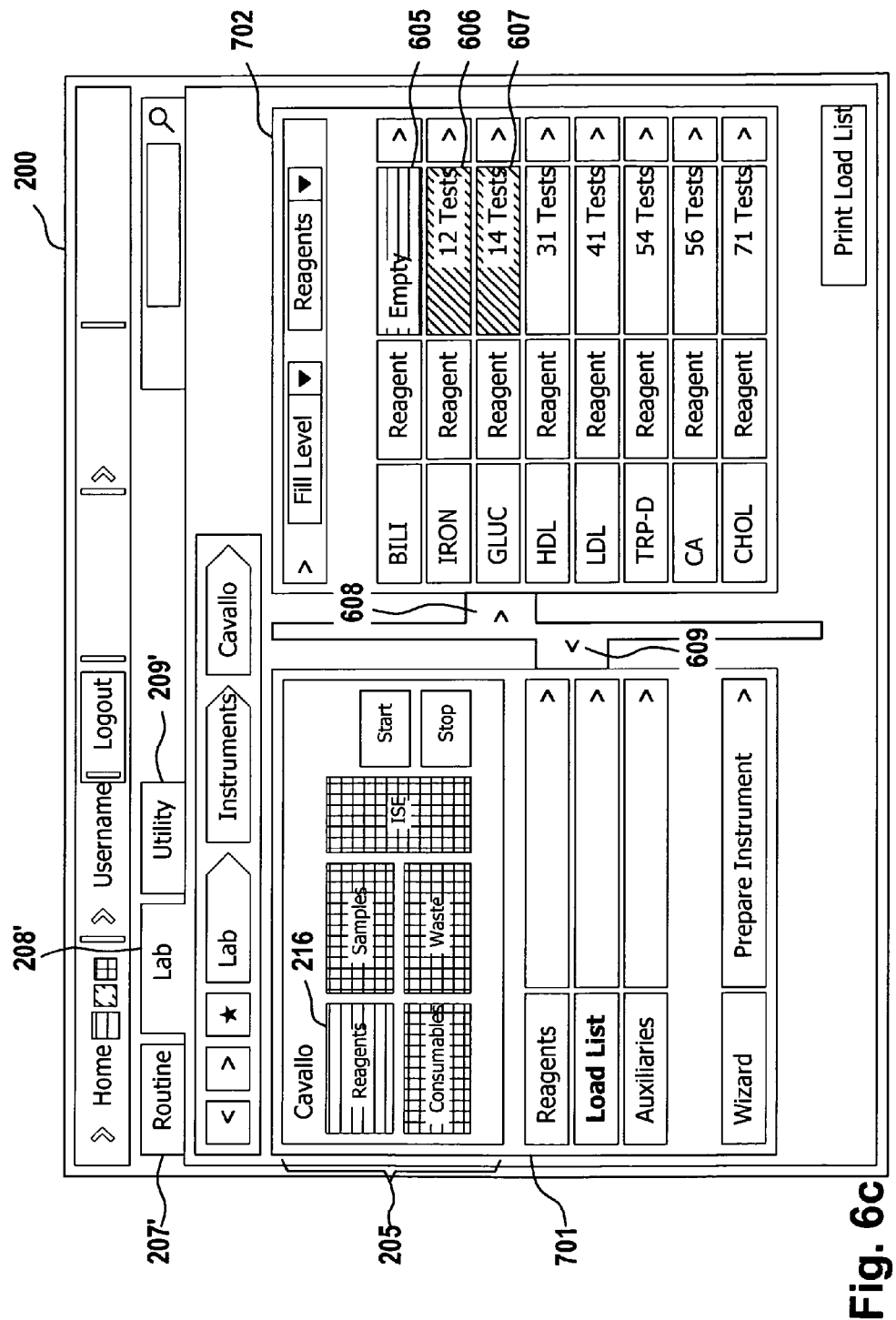

FIGS. 6a-6c illustrate the dynamic specification and aggregated display of tasks. The dynamic specification of new tasks depending on current system state can allow a user working for example on some routine tasks to be informed immediately on a critical system state or a failure of a lab device which requires immediate intervention by the user.

FIG. 6a illustrates a graphical user interface resulting from selecting 'Routine' as current category and from selecting the node 902 'Orders' (see FIG. 9) within the corresponding 'Routine' drill-down graph. On the left side of the pane, a list of orders and corresponding status can be displayed. By selecting, for example, GUI element 601 corresponding to order ID 2, the details of the selected order can be displayed in the 'order details' pane on the right side of the GUI and can be evaluated and verified by the user.

The server computer can constantly receive status information of lab devices belonging to the analysis system connected to the server computer. Such status information can include error codes, messages on used up consumables and the like. In case a lab device runs out of reagents, a new task data object can be dynamically created. The task data object can be indicative of the task to refill the reagent. Depending on the embodiment, different forms of warnings can then be presented to the user, for example, in the form of an acoustic signal and/or in the form of a refresh of the GUI, in particular of the group of squares 202. A user can navigate to the overview pane 201 which is depicted in FIG. 6b. The overview pane can provide the user with an aggregated view of tasks assigned a high urgency level, including the dynamically created task for refilling empty reagent bottles in Cavallo. The GUI element 602 in the tasks area can represent the task of refilling a reagent required for a bilirubine analysis. By selecting GUI element 601, a user can trigger the display of data required for executing the tasks. As a result, the GUI elements contained in the lab device area 205 can be displayed. GUI element 216 in the lab device area can indicate that at least one reagent of the lab device Cavallo needs to be refilled. GUI elements 603, 604 and 216 can be displayed in red color, thereby indicating that the reagent needs to be replaced immediately. By selecting the GUI element 216 representing the reagents subunit of Cavallo, a user can trigger the display of further details as depicted in FIG. 6c. The content of the lab device area 205, in FIG. 6b formerly displayed on the right half of the GUI, is depicted in the detailed view in FIG. 6c on the left half of the GUI. In pane 701, a list of reagents currently loaded in Cavallo can be displayed. The empty reagent bottle for the BILI reagent can be indicated to the user in red color of GUI element 605. Other reagents which may need to be refilled in the near future can be represented as yellow colored GUI elements 606, 607. The list of reagents displayed in pane 702 can be dynamically updated.

Figure 7A:
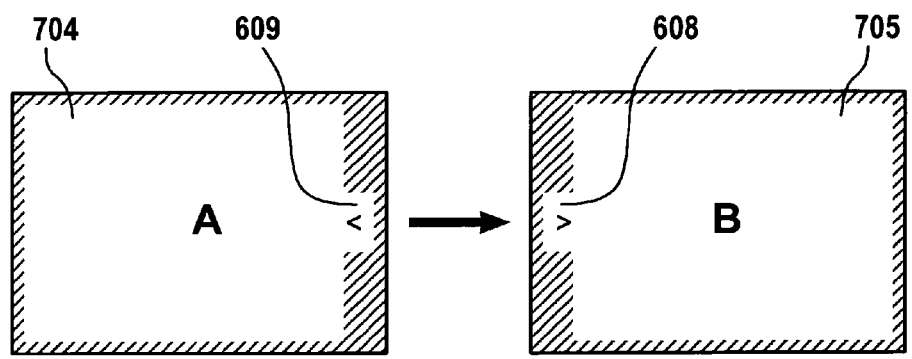
FIG. 7a illustrates an aggregated view displayed according to a first display mode according to an embodiment of the present disclosure.

FIG. 7a depicts an aggregated view generated as the result of a drill-down analysis to the user according to a first display mode. According to the first display mode, the GUI can comprise a first pane 704 or a second pane 705. Each of the panes can be approximately screen size. Each GUI element displayed in the first or second pane can be provided according to a first GUI element version. The version can correspond to a design specially adapted for the display of a GUI element on a small screen, in particular, a screen of a mobile device. "Specially adapted" can imply that the size and resolution of the displayed GUI elements can allow the immediate recognition and comprehension by a user when presented to the user on a small screen. Each GUI element can be a pointer to a node in the drill-down graph. At least one GUI element belonging to the first version of GUI elements can be displayed in the first pane 704. Upon selection of the at least one first GUI element, the node pointed at by the selected GUI element can be used as current node and a drill-down analysis can be executed for the current node. One or more second GUI elements generated as the result of the drill-down analysis can be displayed in the second pane 705. The second pane can be approximately screen size. The second GUI elements can also be provided according to the first GUI element version specially for displaying GUI elements on a small screen. The second pane can replace the first pane, thereby reducing the total amount of GUI elements to be displayed to the user at the same time on a small screen.

Figure 7B:
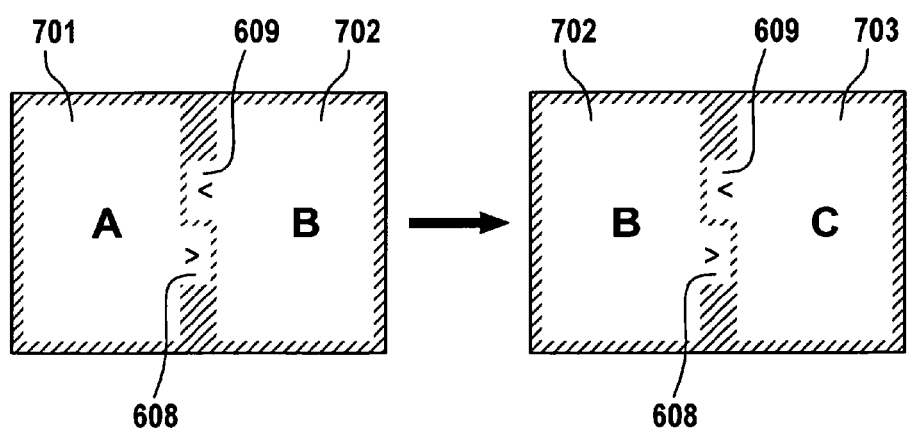
FIG. 7b illustrates an aggregated view generated as the result of a drill-down analysis to the user according to a second display mode according to an embodiment of the present disclosure.

FIG. 7*b* depicts an aggregated view according to a second display mode. According to the second display mode, the GUI can comprise a first pane 701 and a second pane 702, each of the panes can be approximately half screen size. Each GUI element displayed in the first or second pane can be provided according to a second GUI element version. The version can correspond to a design specially adapted for the display of a GUI element on a medium sized screen, in particular, a screen of a computer system or touch screen of a lab device. "Specially adapted" can imply that the size and shape of the displayed GUI elements can allow the immediate recognition and comprehension by a user when presented to the user on a medium-sized screen.

Each GUI element 214-220, 406-410, 430-432 can be a pointer to a node in the drill-down graph (see for example FIGS. 4*a* and 4*b*). At least one second version GUI element can be displayed in the first pane 701, for example, an aggregation GUI element. Upon selection of the at least one first GUI element, the node pointed at by the selected GUI element can be used as current node and a drill-down analysis can be executed for the current node. One or more second GUI elements generated as the result of the drill-down analysis can be displayed in the second pane 702, the second pane can be approximately half screen size. The second GUI elements can also be provided according to the second GUI element version specially adapted for displaying GUI elements on a medium-sized screen. The first and the second pane can be displayed to the user on the left and right side of the GUI at the same time. In case a user navigates further down in the drill-down graph, pane 702 displayed on the right side of the screen depicted in FIG. 6*c* and the left side of FIG. 7*b* can be moved to the left side of the screen, thereby replacing pane 701 while the right side of the screen can display the new pane 703.

FIG. 6*c* corresponds to the second display mode according to which the first pane 701 and the second pane 702 can be displayed simultaneously. The pagination GUI elements 608, 609 can indicate that the content of the first and second pane can be changed by a user executing a drill-down analysis in a way similar to leafing through a book.

FIG. 8*a* depicts a first pane 704 displayed on a screen of a mobile device 106 according to the first display mode. The first pane can comprise the tasks pane and the favorites pane. Upon selection of the aggregation GUI element 132 corresponding to the shared task step of refilling reagents on Cavallo and Cane, a drill-down analysis can be executed and the first pane 704 can be replaced by the second pane 705 as displayed in FIG. 8*b*.

Figure 9:
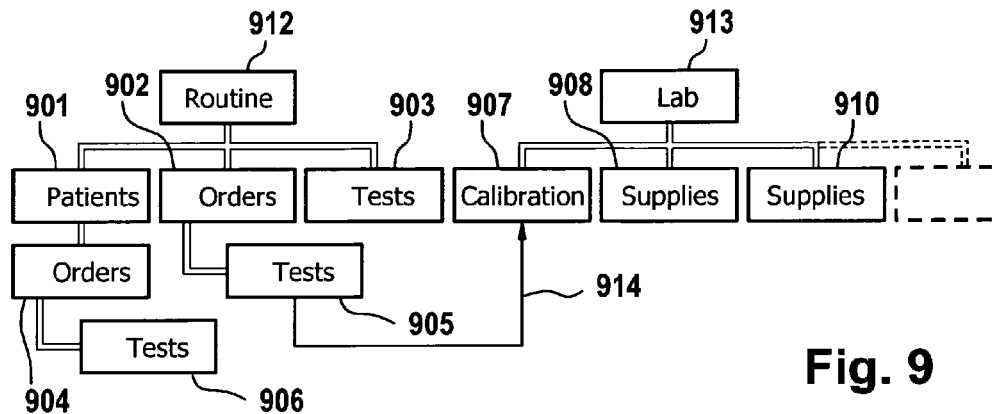
FIG. 9 illustrates parts of two different drill-down graphs corresponding to the categories 'Routine' and 'Lab', the drill-down graphs connected via a link according to an embodiment of the present disclosure.

FIG. 9 depicts parts of two different drill-down graphs corresponding to the categories 'Routine' and 'Lab.' The drill-down graphs can be connected via a link 914. Each box in FIGS. 9 and 10*a* can represent a node 901-913, 1001-1008 in a drill-down graph. Upon selection of tab 207', the drill-down graph having node 912 as root node can be selected as drill-down graph. Accordingly, each of the tabs 207'-209' can provide a user with different entry points for executing a drill-down analysis according to a particular graph topology. Each topology can correspond to a different view of the data contained in the received task data objects added to the nodes of the drill-down graphs.

Figure 10A:
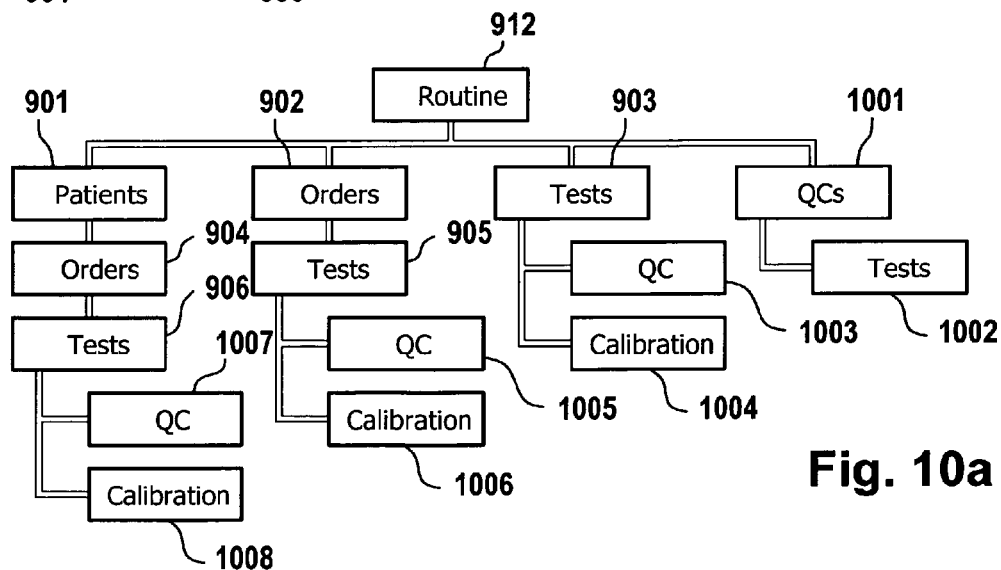
FIG. 10a illustrates an illustration of the drill-down graph corresponding to the category 'Routine' according to an embodiment of the present disclosure.

FIG. 10*a* is a detailed illustration of the drill-down graph corresponding to the category 'Routine'. As can be seen from FIG. 10*a*, multiple drill-down analyses can be executed starting from root node 912 and ending in a "Calibration" node 1004, 1006, 1008. According to a first pathway, the "Calibration" node 1008 can be reached via nodes 912, 901, 904 and 906. According to alternative second pathway, the "Calibration" node 1006 can be reached via nodes 912, 902 and 905.

Figure 10B:
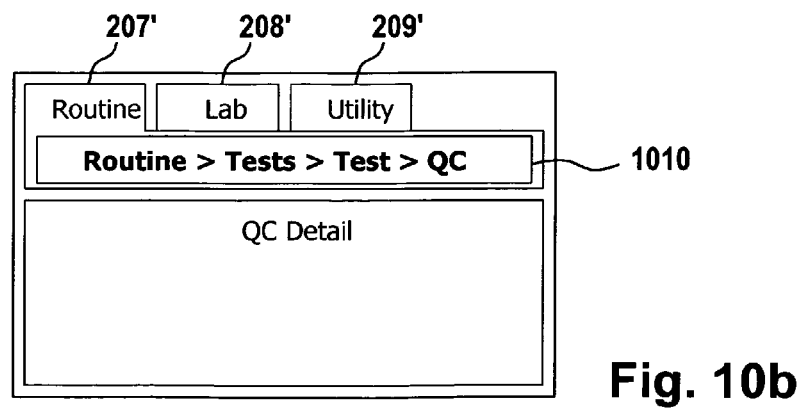
FIG. 10b illustrates the relation between navigational path displayed to the user and the topology of the corresponding drill-down graph according to an embodiment of the present disclosure.

FIG. 10*b* illustrates the relation between the navigation path 500 and 1010 and the corresponding path within the drill-down graph chosen for executing a drill-down analysis. The nodes 912 and 903 belonging to the third branch of the drill-down graph depicted in FIG. 10*a* can correspond to the navigation path 1010 depicted in FIG. 10*b* after a user selected a particular quality control node "QC" for executing a quality check on measurement data received during the execution of a test.

FIG. 11 is a block diagram of an embodiment of an analysis system 100. The analysis system 100 can comprise various lab devices 102.1, 102.2 coupled to a server computer 108 that can control operation of the lab devices. According to the depicted embodiment, at least some of the lab devices can comprise a processor 116.1, 116.2 for executing computer-implemented instructions 118.1, 118.2 which can allow the specification of task data objects and/or can be required for exchanging data with the server computer. Depending on the implementation, at least some of the lab devices can be coupled to the server computer 108 via the network 110. In one embodiment, the analysis system 100 can have a connected lab device A and a connected lab device B. The connected lab device A can have at least one processor 116.1 for execution of program instructions 118.1. The connected lab devices can have a network interface 120.1, 120.2 for coupling the connected lab device A, B to the network 110, in particular in order to enable communication with a server computer 108. The unconnected lab device 180 can be, for example, a refrigerator, a storage room for storing reagents or samples and the like.

The connected lab device A can have a display, such as a computer monitor 122.1 for displaying a screen image 124.1 that may include a textual output. Further, the connected lab device A can have a user identification component 101.1 and a device identification component 103.1. The user identification component 101.1 can serve for identification of a human user 104, such as a laboratory assistant. The user identification component 101.1 can be for the user's 104 entry of his user name and password. Alternatively or in addition, the user identification component 101.1 can implement an RFID method for determining the user's 104 identity by an RFID chip card of that user. As an alternative or in addition, the user identification component 101.1 can be operable to perform the user's 104 identification using a biometric method, such as fingerprint identification. In this instance, the user identification component 101.1 can comprise a sensor for sensing the user's 104 respective biometric features, such as a fingerprint sensor. The device identification component 103.1 can be a protected storage area of the connected lab device A in which a unique device identifier for identification of the device can be stored. This device identifier can be a serial number, such as a globally unique identifier (GUID) that can be assigned to the connected lab device A during its production or it can be an identifier that can be unique within the analysis system and that can be assigned to the connected lab device A by an administrator of the analysis system. Alternatively, the device ID may not be permanently stored by the device identification component 103.1 but the device ID can be computed by the device identification component 103.1 each time an identification of the connected lab device A is required. The computation of the device ID can be executed by the device identification component 103.1 using a predefined algorithm, such as a cryptographic algorithm. The connected lab device B of the analysis system 100 can have a design that is analogous to the connected lab device A. Thus, the connected lab device B can have a user identification component 101.2, a device identification component 103.2, a processor 116.2 for execution of program instructions 118.2, a monitor 122.2 for displaying a screen image 124.2 and a metric interface 120.2 corresponding to the respective components of the connected lab device A. The analysis system 100 in addition may comprise one or more unconnected lab devices 180, for example, a refrigerator for storing reagents that can be required for operating the various analyzers of the analysis system 100. It can also be possible to consider whole rooms, in particular storage rooms, as 'unconnected lab device'.

The server computer 108 can have a processor 160 for the execution of program instructions 162, and a network interface 164 for coupling the server computer 108 to the network 110. The instructions 162 can be stored on a computer-readable, non-transitory storage medium, for example, a magneto-electric data storage, a Flash memory or the like. The program instructions 162 can comprise a program module for receiving, creating, modifying and/or deleting task data objects stored in a database, or storage component, 190 coupled to the server computer 108. In operation, the user 104 can log into the analysis system 100, for example, via connected lab device A. By operation of the user identification component 101.1, the user 104 can be identified. The user's 104 identifier and the device identifier of the connected lab device A provided by the device identifier component 103.1 can be sent from the interface 120.1 of the connected lab device A to the server computer 108 via the network 110. This can invoke the execution of the program instructions 162 which can select and process task data objects assigned at least the identifier of the identified user and the device identifier received from the connected lab device A. For example, the program 162 can query database 190 in which the task data objects can be stored using the user identifier and/or the device identifier as a search term.

The signal may likewise be sent to the mobile device 106 of the user 104, whereby the GUI elements displayed to the user can belong to the first version of GUI elements. The mobile device 106 can have an integrated display 130. Further, the mobile device 106 can have a network interface 198 for coupling to the network 110. In operation, the user 104 can select one of the connected lab devices A or B, so that the server computer 108 can receive a user identifier and device identifier. The user identifier and the device identifier can be used by the program 162 to determine one or more task data object to be executed by the user by the database 190.

The signal sent to the mobile device 106 of the user 104 or to any of the lab devices can comprise information regarding the device-id or room-ID where one or more tasks have to be executed. For example, the signal can comprise a set of task data objects indicting that several reagents may need to be refilled and that fresh reagent bottles can be retrieved from the unconnected lab device C 180. Each of the task data objects can comprise information on the room number where the lab device C, in this case a refrigerator, can be found. In case multiple tasks have to be executed by the user in respect to the unconnected lab device, the user can be provided with an aggregated view on the multitude of tasks. Upon receipt of this signal by the mobile device 106, the user 104 can walk to the unconnected lab device C for execution of the determined one or more tasks. After completion of the execution of the determined step the user 104 may use the mobile device 106 in order to acknowledge completion of the execution which can be signalled from the mobile device back to the server computer 108 in order to mark the tasks completed in the database 190.

Figure 12:
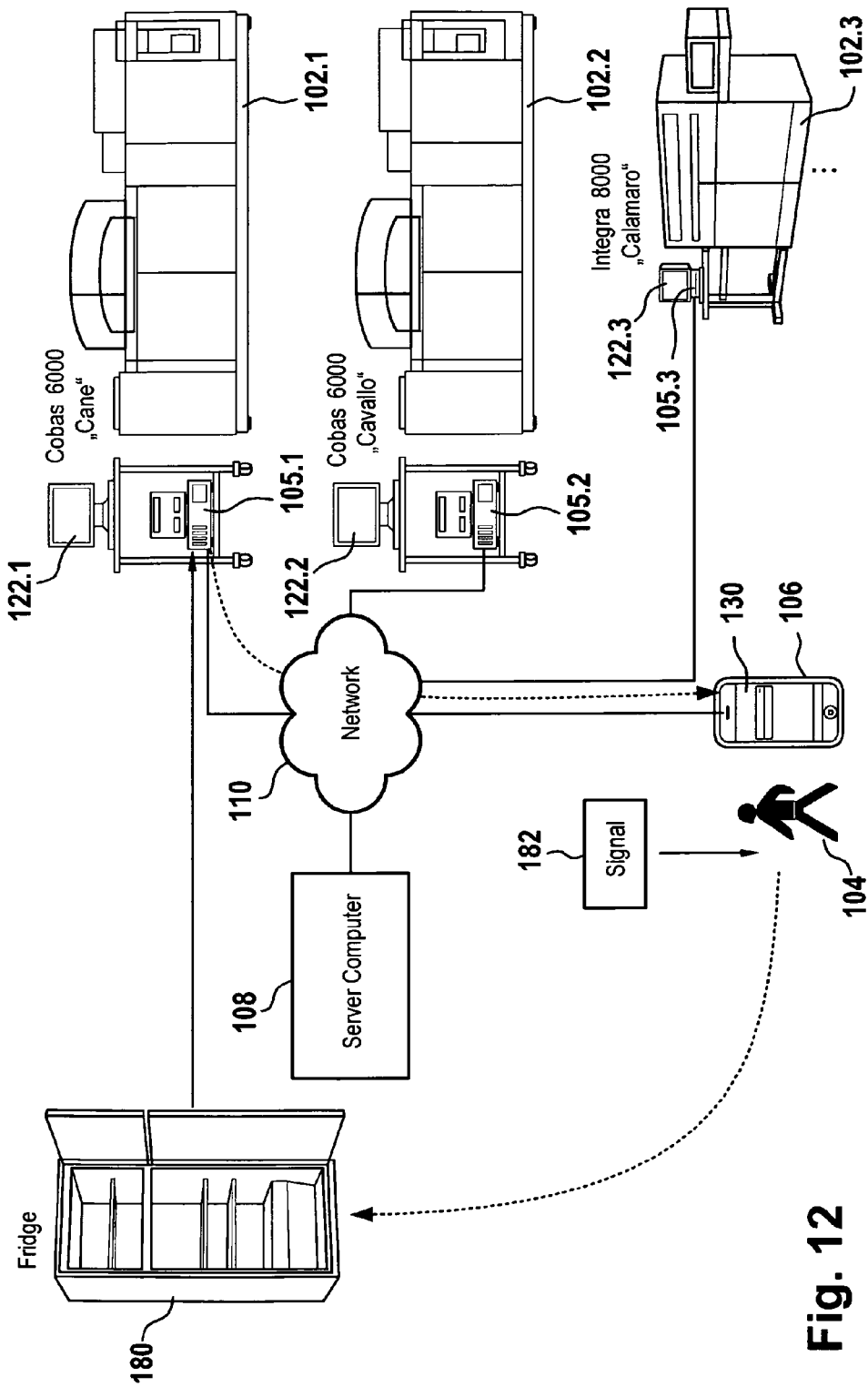
FIG. 12 illustrates a block diagram of an embodiment of an analysis system where the task of refilling a reagent is signalled to a user according to an embodiment of the present disclosure.

FIG. 12 is a block diagram of a further embodiment of an analysis system where the requirement for refilling a reagent can be signalled to a user. The depicted analysis system can comprise an analyser 102.1 of the cobas 6000 type having the device ID 'Cane', analyzer 102.2 of the cobas 6000 type having the device ID 'Cavallo' and analyzer 102.3 of the Integra 800 type having the device ID 'Calamaro'. The analyzer 102.1 and its analyzer control computer 105.1 can constitute connected lab device A and the analyser 102.2 and its analyser control computer 105.2 can constitute connected lab device B. The analysis system can further comprise the unconnected lab device 180 which can be a refrigerator for storing a stock of reagents.

In operation, one of the analyzers, such as the analyser 102.1, can require refilling of a reagent. For example, this can be sensed by a sensor coupled to the analyser control computer 105.1. When the charging level of the reagent of the analyser 102.1 is below a predefined threshold level, the analyser control computer 105.1 can generate a signal 182 that can be sent to the mobile device 106, depending on the embodiment of the invention, either directly or through the intermediary of the server computer 108. According to embodiments wherein the signal 182 is sent directly from the analyzer control computer 105.1 to the mobile device, the analyzer control computer can, in addition to the server computer, execute the aggregating of task data objects as described for the server computer 108 or can receive the results of aggregating the received task data objects from the server computer 108.

Figure 13:
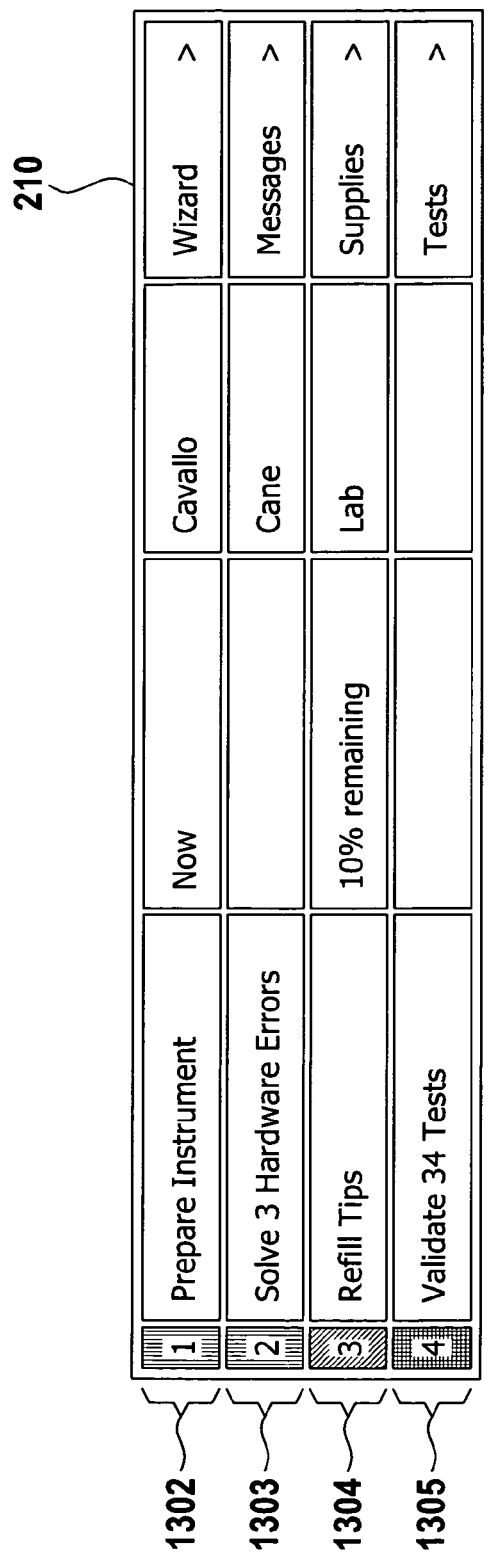
FIG. 13 illustrates a screenshot displaying four GUI elements respectively representing a different aggregated task data object group according to an embodiment of the present disclosure.

FIG. 13 is a screenshot displaying four GUI elements 1302-1305 of four different aggregated task data object groups. The aggregated data value calculated for each aggregated task data object group can be used for specifying each respective GUI element. For example, GUI element 1303 can be indicative of the fact that three hardware errors on lab device 'Cane' which need to be resolved in respective tasks. GUI element 1305 can be indicative of 34 test validation tasks, whereby the number '34' can be the aggregated data value. Aggregation GUI element 1303 can represent three task data objects for managing and resolving hardware errors, whereby the attribute used for aggregating can be an identifier of messages pane 1408. The messages pane 1408 depicted in FIG. 14 can be encoded by a particular set of program instructions which, via the messages pane, can allow executing tasks related to the maintenance of the devices. Accordingly, all task data objects representing tasks related to the maintenance of lab devices which can be resolved by messages pane 1408 can be assigned an attribute indicative of messages pane 1408 and used for aggregating the task data objects. In addition, the aggregation of task data objects providing the GUI elements 1303-1407 can be based on a further attribute indicative of a physical location, in this case the lab device at which a maintenance task may need to be executed. For example, GUI 1303 can be indicative of maintenance tasks for the device Cane while GUI element 1401 can be indicative of maintenance tasks related to the device 'Cobas 4000'. Aggregation GUI element 1304 can be indicative of a plurality of supply-related tasks. All task data objects represented by GUI element 1304 can be assigned an attribute indicative of the supply pane 1505, whereby the supply pane 1505 can provide a user with a method for recognizing and/or resolving the aggregated supply-related tasks.

Figure 14:
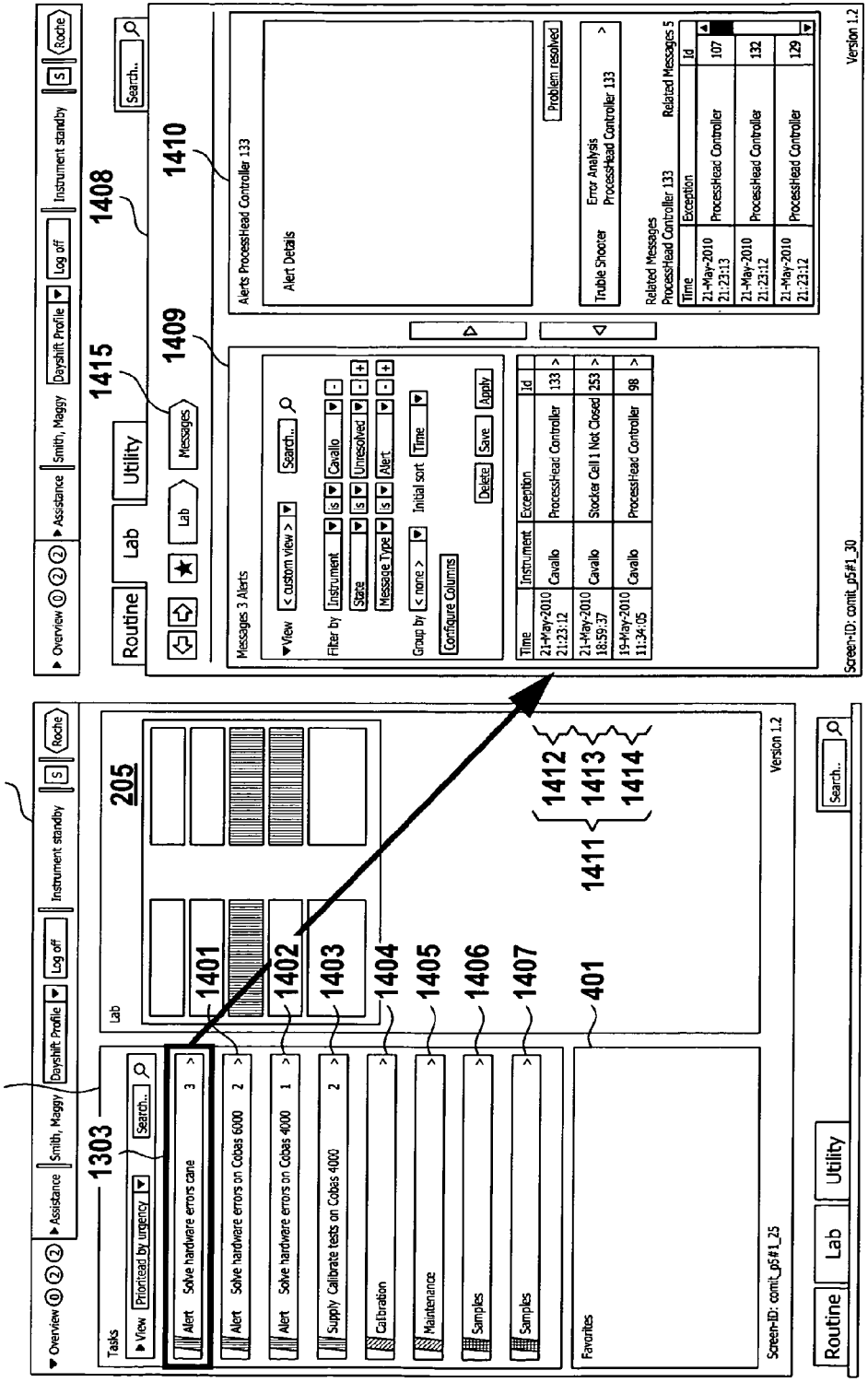
FIG. 14 illustrates a screenshot of two window panes displaying and/or executing maintenance tasks according to an embodiment of the present disclosure.

FIG. 14 is a screenshot of two window panes for displaying and resolving tasks related to hardware problems of lab devices. The left window pane can comprise a favorites area 401, a lab device area 205, and a tasks area 210. Each GUI element 1303-1407 can be implemented as selectable aggregation GUI element and can be indicative of its number of aggregated task data objects. Upon selection of the aggregation GUI elements, for example, element 1303, a workflow execution view comprising message pane 1408 suitable for executing the tasks represented by the GUI element 1303 can be displayed in the right half of the screen. The function of messages pane 1408 can be to provide a user with all information necessary to resolve the tasks represented by GUI element 1303. Messages pane 1408 can comprise a messages area 1409, a non-aggregated task list 1411 and an alert details area 1410. The non-aggregated tasks list 1411 can display a list of tasks GUI elements 1412-1414 respectively representing singular tasks. The tasks can be collectively represented by aggregation GUI element 1303. Each task of the list 1411 can comprise additional information such as the lab device submitting the alert, the type of alert and/or the type of component of the lab device where the failure occurred, a task ID, and the time and date when the alert was submitted. The user can select the task GUI elements, for example, 1412. As a result, alert details area 1410 can display additional information assisting a user in resolving the detected hardware problems.

Figure 15:
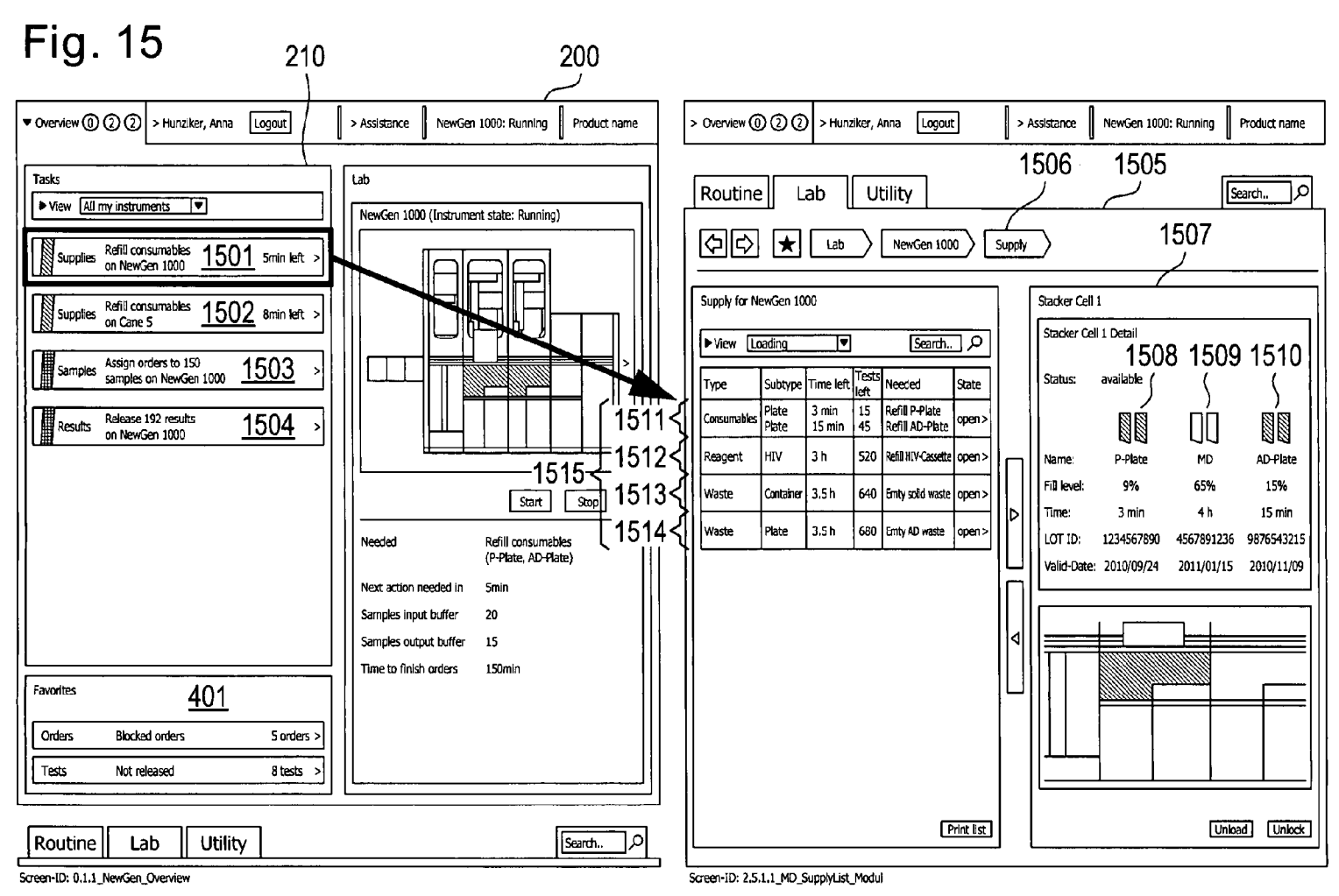

FIG. 15 is a screenshot of two window panes for displaying and resolving supply related tasks. The left pane of the window can comprise a tasks area 210, a lab device area 205 displaying the lab device 'NewGen 100' and its components, and a favorites area 401. Lab device area 205 can comprise a list of aggregation GUI elements 1501-1504. The aggregation of task data objects can be based on shared attributes which can be indicative of program instructions for resolving the corresponding task. For example, program instructions can specify a task execution view comprising a supply pane 1505 for assisting a user in resolving supply related tasks. The aggregation GUI elements 1501-1504 can be based on a shared attribute indicative of a physical location, in this case the lab device at which a supply task may need to be executed. For example, GUI 1501 can be indicative of supply tasks for the device NewGen 1000 while GUI element 1502 can be indicative of supply tasks related to the device 'Cane'. A user, by clicking on aggregation GUI element 1501, can trigger the display of supply pane 1505. The supply pane can comprise a non-aggregated task list 1515 and a supply status details pane 1507. The non-aggregated list can comprise task GUI elements 1511-1514 respectively representing a maintenance task. A user, by selecting a particular task GUI element 1511 can trigger the display of task related details in the supply status details pane 1507. The supply details area can comprise GUI elements 1508-1510 indicating the supply status of components of the device NewGen 1000.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An analysis system for analyzing biological samples, the analysis system comprising:
   a lab device;
   a server having a server interface component for receiving task data objects, each task data object comprising an attribute, wherein at least some of the received task data objects are indicative of a laboratory procedure to be performed by the lab device and wherein each task data object is assigned an urgency level attribute, the server comprising,
   a processing component for
   aggregating at least some of the received task data objects into aggregated task data object groups, wherein all task data objects belonging to the same aggregated task data object group share an attribute value or value range of the attribute, the shared attribute value or value range indicative of at least one shared step of the task of the attribute's task data object, the shared step being shared by all tasks of the task data objects of the aggregated task data object group, wherein each aggregated task data object group is assigned an aggregated urgency level value, the aggregated urgency level value being calculated as the maximum urgency level attribute value assigned to any of the task data objects within the aggregated task data object group,
   specifying a selectable aggregation GUI element for each of the aggregated task data object groups, the aggregation GUI element representing the aggregated task data object group,
   displaying the aggregation GUI elements in an aggregated view, wherein the aggregated view is a view comprising at least one aggregated task data object of those aggregated task data object groups whose aggregated urgency level value is above a first threshold,
   notifying one or more users if the aggregated urgency level value is above a second threshold in order to preserve operability of the analysis system, and upon selection of the aggregation GUI elements by a user, selecting the aggregated task data object group represented by the selected aggregation GUI element and automatically providing the user access to program instructions for executing the shared step of the selected aggregated task data object group; and a graphical user interface for displaying the specified aggregation GUI elements for providing the aggregated view.

2. The analysis system according to claim 1, wherein a device-ID is assigned to some of the received task data objects, each device-ID being indicative of the lab device, wherein the lab device comprises a device identification component for identifying the lab device at the server via a device-ID, and wherein the server comprises a service interface component, wherein the service interface component sends a signal to the identified lab device via the service interface component, the signal comprising data aggregated on the received task data objects to which is assigned the device-ID of the identified lab device.

3. A method implemented by an analysis system, the analysis system being used for processing biological samples, the method comprising:

receiving task data objects, each task data object comprising an attribute, wherein some of the received task data objects are indicative of a laboratory procedure to be performed by the lab device, the lab device belonging to the analysis system, wherein each task data object is assigned an urgency level attribute;

aggregating at least some of the received task data objects into aggregated task data object groups, wherein all task data objects belonging to the same aggregated task data object group share an attribute value or value range of the attribute, the shared attribute value or value range being indicative of a shared step of the task of the attribute's task data object, the shared step being shared by all tasks of the task data objects of the aggregated task data object group, wherein each aggregated task data object group is assigned an aggregated urgency level value, the aggregated urgency level value being calculated as the maximum urgency level attribute value assigned to any of the task data objects within the aggregated task data object group;

specifying a selectable aggregation GUI element for each of the aggregated task data object groups, the aggregation GUI element representing the aggregated task data object group;

displaying the aggregation GUI elements in an aggregated view on a graphical user interface, wherein the aggregated view is a view comprising at least one aggregated task data object of those aggregated task data object groups whose aggregated urgency level value is above a first threshold;

notifying one or more users if the aggregated urgency level value is above a second threshold in order to preserve operability of the analysis system; and upon selection of aggregation GUI elements by a user, selecting the aggregated task data object group represented by the selected aggregation GUI element and automatically providing the user access to program instructions for executing the shared step of the selected aggregated task data object group.

4. The method according to claim 3, wherein a hierarchical drill-down graph comprising at least two hierarchical levels and comprising one or more first nodes is used for aggregating the task data objects, each first node having assigned a node attribute.

5. The method according to claim 4, further comprising, representing each received task data object as a second node of the hierarchical drill-down graph.

6. The method according to claim 4, further comprising, storing, for each drill-down analysis, the aggregated data value in a drill-down history, the drill-down history being stored in a working memory; and selecting a navigation GUI element by a user, the user thereby selecting a new current node, the new current node corresponding to a previously executed drill-down analysis.

7. The method according to claim 4, further comprising:

providing each of the aggregation GUI elements according to a first aggregation GUI element version, each GUI element version corresponding to a particular graphical design, the first GUI element version being displayed on a small screen, wherein each aggregation GUI element is a pointer to one of the first nodes in the drill-down graph;

displaying the aggregated view comprising the aggregation GUI elements in a first pane, the first pane approximately screen size; and displaying a second pane approximately screen size, the second pane replacing the first pane, the second pane comprising:

one or more further aggregation GUI elements, or one or more task GUI elements, each task GUI element representing a task data object of an aggregated task data object group represented by one of the aggregation GUI elements of the first pane, wherein upon selection of any of the task GUI elements, instructions for executing the shared step of the one aggregated task data object group are executed.

8. The method according to claim 7, wherein the small screen is a screen of a mobile user device.

9. The method according to claim 7, wherein the content of the second pane is constructed by, upon selection of the aggregation GUI elements in the first pane, selecting one of the first nodes of the drill-down graph as current node;

executing a drill-down analysis, the drill-down analysis being a data aggregation operation executed on the current node and all direct and indirect successor nodes of the current node, wherein when executing the aggregation operation on the nodes, the node attribute of the current node is used in the aggregation operation as aggregation attribute in accordance with the aggregating at least some of the received task data objects into aggregated task data object groups, wherein further aggregation task data object groups are created;

representing each of the further aggregated task data object groups by the further aggregation GUI elements.

10. The method according to claim 3, further comprising, monitoring the status of the lab device to receive status information of the lab device;

dynamically creating, modifying and/or deleting some of the received task data objects depending on the received status information; and triggering a re-execution of the aggregating some of the received task data objects into aggregated task data object groups, the specifying a selectable aggregation GUI element for each of the aggregated task data object groups, the displaying the aggregation GUI elements in an aggregated view, and the upon selection of one of the aggregation GUI elements by a user, selecting the aggregated task data object group represented by the selected aggregation GUI element and automatically providing the user access to program instructions for executing the shared step of the selected aggregated task data object group, wherein as a result of the re-execution a dynamically updated, aggregated view of tasks to be executed is provided.

11. The method according to claim 3, wherein the task data objects of the selected aggregated task data object group respectively represent a task of inspecting and/or validating a measurement result, wherein providing the user access to program instructions for executing the step shared by all the tasks comprises displaying a workflow-execution view, the workflow execution view comprising one or more task execution GUI elements enabling the user to inspect and/or validate the measurement results, and wherein the shared step of the selected aggregated task data object group is the automatically selecting the workflow execution view from a plurality of workflow execution views for display.

12. The method according to claim 11, further comprising,
receiving, via the workflow execution view, a confirmation signal indicative of an approval of one of the measurement results by the user; and
in the case of having received the confirmation signal, automatically forwarding or making available the result to a LIS or a middleware component.

13. The method according to claim 3, wherein the lab device is one of a plurality of lab devices, wherein the task data objects of the selected aggregated task data object group respectively represent a maintenance task of maintaining one of the plurality of lab devices, and wherein providing the user access to program instructions for executing the step shared by all the tasks comprises displaying a workflow-execution view, the workflow execution view comprising one or more task execution GUI elements, each task execution GUI element comprising information on a current state of one of the lab devices and/or information on how to repair the lab device.

14. The method of claim 13, wherein the shared step of the selected aggregated task data object group is selected from the group comprising,
executing the maintenance tasks at a shared location, the shared location being shared by all lab devices whose maintenance tasks are aggregated within the selected aggregated task data object group;
selecting the workflow execution view from a plurality of workflow execution views for display; and
retrieving one or more consumables from a shared location for making the respective lab device operative, the shared location being shared by all lab devices whose maintenance tasks are aggregated within the selected aggregated task data object group.

15. The method according to claim 13, further comprising,
receiving, via the workflow execution view, a confirmation signal indicative of a successful maintenance by the user; and
if the confirmation signal was received, automatically sending a command to each of the lab devices for which the confirmation signal was received, thereby automatically activating the lab device and enabling the lab device to execute its respective laboratory procedure.

16. The method according to claim 3, wherein the lab device is one of a plurality of lab devices, wherein the task data objects of the selected aggregated task data object group respectively represent a task of transporting one or more biological samples having been processed by one of the lab devices from any of the lab devices to a destination location, wherein the shared step of the selected aggregated task data object group is the transporting the one or more biological samples to a shared destination location, wherein providing the user access to program instructions for executing the shared step comprises displaying a workflow-execution view, and automatically triggering, upon receiving via the workflow execution view a confirmation signal indicative of a confirmation for the destination location by the user, one or more robotic units to automatically execute the confirmed transportation tasks of the selected aggregated task data object group, thereby transporting each of the biological samples processed by any of the lab devices to the shared destination location.

* * * * *